United States Patent
Yu et al.

(10) Patent No.: US 11,724,097 B2
(45) Date of Patent: Aug. 15, 2023

(54) SYSTEM AND METHOD FOR CONTROLLING THE POSITION OF A LEVITATED ROTOR

(71) Applicant: TC1 LLC, Pleasanton, CA (US)

(72) Inventors: Shunzhou Yu, Ann Arbor, MI (US); Alexander Medvedev, Ann Arbor, MI (US); Ren You, Windsor (CA)

(73) Assignee: TC1 LLC, St. Paul, MN (US)

( * ) Notice: Subject to any disclaimer, the term of this patent is extended or adjusted under 35 U.S.C. 154(b) by 108 days.

(21) Appl. No.: 17/135,416

(22) Filed: Dec. 28, 2020

(65) Prior Publication Data

US 2021/0187275 A1 Jun. 24, 2021

Related U.S. Application Data

(63) Continuation of application No. 16/218,791, filed on Dec. 13, 2018, now Pat. No. 10,874,782, which is a
(Continued)

(51) Int. Cl.
*A61M 60/824* (2021.01)
*A61M 60/422* (2021.01)
(Continued)

(52) U.S. Cl.
CPC ........ *A61M 60/824* (2021.01); *A61M 60/178* (2021.01); *A61M 60/232* (2021.01);
(Continued)

(58) Field of Classification Search
CPC .. A61M 60/422; A61M 60/50; A61M 60/824; A61M 2205/3317
See application file for complete search history.

(56) References Cited

U.S. PATENT DOCUMENTS

| | | |
|---|---|---|
| 1,093,868 A | 4/1914 | Leighty |
| 2,684,035 A | 7/1954 | Kemp |
| | (Continued) | |

FOREIGN PATENT DOCUMENTS

| | | |
|---|---|---|
| CN | 1347585 A | 5/2002 |
| CN | 1462344 A | 12/2003 |
| | (Continued) | |

OTHER PUBLICATIONS

Asama, J., et al., "A Compact Highly Efficient and Low Hemolytic Centrifugal Blood Pump With a Magnetically Levitated Impeller", Artificial Organs, vol. 30, No. 3, Mar. 1, 2006 (Mar. 1, 2006), pp. 160-167.
(Continued)

*Primary Examiner* — George R Evanisko
(74) *Attorney, Agent, or Firm* — Kilpatrick Townsend & Stockton LLP

(57) ABSTRACT

A rotary machine is provided which may include a rotor and a stator within a housing. The stator may be for generating a rotating magnetic field for applying a torque to the rotor. A commutator circuit may provide a plurality of phase voltages to the stator, and a controller may adjust the plurality of phase voltages provided by the commutator circuit to modify an attractive force of the stator on the rotor to move the rotor in an axial direction.

17 Claims, 16 Drawing Sheets

Related U.S. Application Data continuation of application No. 15/042,431, filed on Feb. 12, 2016, now Pat. No. 10,166,318.

(60) Provisional application No. 62/115,324, filed on Feb. 12, 2015, provisional application No. 62/115,603, filed on Feb. 12, 2015.

(51) Int. Cl.
*A61M 60/822* (2021.01)
*A61M 60/232* (2021.01)
*A61M 60/237* (2021.01)
*A61M 60/538* (2021.01)
*A61M 60/178* (2021.01)
*A61M 60/148* (2021.01)

(52) U.S. Cl.
CPC ........ *A61M 60/237* (2021.01); *A61M 60/422* (2021.01); *A61M 60/538* (2021.01); *A61M 60/822* (2021.01); *A61M 60/148* (2021.01); *A61M 2205/3306* (2013.01); *A61M 2205/3317* (2013.01); *A61M 2205/3334* (2013.01)

(56) References Cited

U.S. PATENT DOCUMENTS

| | | |
|---|---|---|
| 3,023,334 A | 2/1962 | Burr et al. |
| 3,510,229 A | 5/1970 | Smith |
| 3,620,638 A | 11/1971 | Kaye et al. |
| 3,870,382 A | 3/1975 | Reinhoudt |
| 3,932,069 A | 1/1976 | Giardini et al. |
| 3,960,468 A | 6/1976 | Boorse et al. |
| 4,149,535 A | 4/1979 | Voider |
| 4,382,199 A | 5/1983 | Isaacson |
| 4,392,836 A | 6/1983 | Sugawara |
| 4,434,389 A | 2/1984 | Langley et al. |
| 4,507,048 A | 3/1985 | Belenger et al. |
| 4,528,485 A | 7/1985 | Boyd, Jr. |
| 4,540,402 A | 9/1985 | Aigner |
| 4,549,860 A | 10/1985 | Yakich |
| 4,645,961 A | 2/1987 | Maisky |
| 4,686,982 A | 8/1987 | Nash |
| 4,688,998 A | 8/1987 | Olsen et al. |
| 4,753,221 A | 6/1988 | Kensey et al. |
| 4,763,032 A | 8/1988 | Bramm et al. |
| 4,769,006 A | 9/1988 | Papatonakos |
| 4,779,614 A | 10/1988 | Moise |
| 4,790,843 A | 12/1988 | Carpentier et al. |
| 4,806,080 A | 2/1989 | Mizobuchi et al. |
| 4,817,586 A | 4/1989 | Wampler |
| 4,846,152 A | 7/1989 | Wampler et al. |
| 4,857,781 A | 8/1989 | Shih |
| 4,888,011 A | 12/1989 | Kung et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,964,864 A | 10/1990 | Summers et al. |
| 4,969,865 A | 11/1990 | Hwang et al. |
| 4,985,014 A | 1/1991 | Orejola |
| 4,995,857 A | 2/1991 | Arnold |
| 5,021,048 A | 6/1991 | Buckholtz |
| 5,078,741 A | 1/1992 | Bramm et al. |
| 5,092,844 A | 3/1992 | Schwartz et al. |
| 5,092,879 A | 3/1992 | Jarvik |
| 5,100,374 A | 3/1992 | Kageyama |
| 5,106,263 A | 4/1992 | Irie |
| 5,106,273 A | 4/1992 | Lemarquand et al. |
| 5,106,372 A | 4/1992 | Ranford |
| 5,112,202 A | 5/1992 | Ozaki et al. |
| 5,129,883 A | 7/1992 | Black |
| 5,145,333 A | 9/1992 | Smith |
| 5,147,186 A | 9/1992 | Buckholtz |
| 5,112,349 A | 12/1992 | Summers et al. |
| 5,190,528 A | 2/1993 | Fonger et al. |
| 5,201,679 A | 4/1993 | Velte et al. |
| 5,211,546 A | 5/1993 | Isaacson et al. |
| 5,229,693 A | 7/1993 | Futami et al. |
| 5,275,580 A | 1/1994 | Yamazaki |
| 5,290,227 A | 1/1994 | Pasque |
| 5,360,445 A | 1/1994 | Goldowsky |
| 5,290,236 A | 3/1994 | Mathewson |
| 5,300,112 A | 4/1994 | Barr |
| 5,306,295 A | 4/1994 | Kolff et al. |
| 5,312,341 A | 5/1994 | Turi |
| 5,313,128 A | 5/1994 | Robinson et al. |
| 5,332,374 A | 7/1994 | Kricker et al. |
| 5,346,458 A | 9/1994 | Afield |
| 5,350,283 A | 9/1994 | Nakazeki et al. |
| 5,354,331 A | 11/1994 | Schachar |
| 5,370,509 A | 12/1994 | Golding et al. |
| 5,376,114 A | 12/1994 | Jarvik |
| 5,385,581 A | 1/1995 | Bramm et al. |
| 5,405,383 A | 11/1995 | Barr |
| 5,449,342 A | 12/1995 | Hirose et al. |
| 5,478,222 A | 12/1995 | Heidelberg et al. |
| 5,504,978 A | 4/1996 | Meyer, III |
| 5,507,629 A | 4/1996 | Jarvik |
| 5,519,270 A | 5/1996 | Yamada et al. |
| 5,533,957 A | 9/1996 | Aldea |
| 5,569,111 A | 10/1996 | Cho et al. |
| 5,575,630 A | 11/1996 | Nakazawa et al. |
| 5,588,812 A | 12/1996 | Taylor et al. |
| 5,595,762 A | 1/1997 | Derrieu et al. |
| 5,643,226 A | 1/1997 | Cosgrove et al. |
| 5,611,679 A | 3/1997 | Ghosh et al. |
| 5,613,935 A | 3/1997 | Jarvik |
| 5,630,836 A | 5/1997 | Prem et al. |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,708,346 A | 1/1998 | Schob |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,755,784 A | 5/1998 | Jarvik |
| 5,776,111 A | 7/1998 | Tesio |
| 5,795,074 A | 8/1998 | Rahman et al. |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,749,855 A | 12/1998 | Reitan |
| 5,843,129 A | 12/1998 | Larson et al. |
| 5,851,174 A | 12/1998 | Jarvik et al. |
| 5,853,394 A | 12/1998 | Tolkoff et al. |
| 5,890,883 A | 4/1999 | Golding et al. |
| 5,911,685 A | 6/1999 | Siess et al. |
| 5,917,295 A | 6/1999 | Mongeau |
| 5,917,297 A | 6/1999 | Gerster et al. |
| 5,921,913 A | 7/1999 | Siess |
| 5,924,848 A | 7/1999 | Izraelev |
| 5,924,975 A | 7/1999 | Goldowsky |
| 5,928,131 A | 7/1999 | Prem |
| 5,938,412 A | 8/1999 | Israelev |
| 5,941,813 A | 8/1999 | Sievers et al. |
| 5,945,753 A | 8/1999 | Maegawa et al. |
| 5,868,702 A | 9/1999 | Stevens et al. |
| 5,868,703 A | 9/1999 | Bertolero et al. |
| 5,947,703 A | 9/1999 | Nojiri et al. |
| 5,951,263 A | 9/1999 | Taylor et al. |
| 5,984,892 A | 11/1999 | Bedingham |
| 5,964,694 A | 12/1999 | Siess et al. |
| 6,004,269 A | 12/1999 | Crowley et al. |
| 6,007,479 A | 12/1999 | Rottenberg et al. |
| 6,030,188 A | 2/2000 | Nojiri et al. |
| 6,042,347 A | 3/2000 | Scholl et al. |

(56) References Cited

U.S. PATENT DOCUMENTS

| | | |
|---|---|---|
| 6,053,705 A | 4/2000 | Schob et al. |
| 6,066,086 A | 5/2000 | Antaki et al. |
| 6,071,093 A | 6/2000 | Hart |
| 6,074,180 A | 6/2000 | Khanwilkar et al. |
| 6,080,133 A | 6/2000 | Wampler |
| 6,082,900 A | 7/2000 | Takeuchi et al. |
| 6,083,260 A | 7/2000 | Aboul-Hosn et al. |
| 6,100,618 A | 8/2000 | Schoeb et al. |
| 6,058,593 A | 9/2000 | Siess |
| 6,123,659 A | 9/2000 | leBlanc et al. |
| 6,123,726 A | 9/2000 | Mori et al. |
| 6,139,487 A | 10/2000 | Siess |
| 6,086,527 A | 11/2000 | Talpade |
| 6,142,752 A | 11/2000 | Akamatsu et al. |
| 6,143,025 A | 11/2000 | Stobie et al. |
| 6,146,325 A | 11/2000 | Lewis et al. |
| 6,149,683 A | 11/2000 | Lancisi et al. |
| 6,158,984 A | 12/2000 | Cao et al. |
| 6,171,078 B1 | 1/2001 | Schob |
| 6,176,822 B1 | 1/2001 | Nix et al. |
| 6,176,848 B1 | 1/2001 | Rau et al. |
| 6,179,773 B1 | 1/2001 | Prem et al. |
| 6,190,304 B1 | 2/2001 | Downey et al. |
| 6,200,260 B1 | 3/2001 | Bolling |
| 6,206,659 B1 | 3/2001 | Izraelev |
| 6,254,359 B1 | 3/2001 | Aber |
| 6,222,290 B1 | 4/2001 | Schob et al. |
| 6,227,797 B1 | 5/2001 | Watterson et al. |
| 6,227,820 B1 | 5/2001 | Jarvik |
| 6,234,772 B1 | 5/2001 | Wampler et al. |
| 6,234,998 B1 | 5/2001 | Wampler |
| 6,247,892 B1 | 6/2001 | Kazatchkov et al. |
| 6,249,067 B1 | 6/2001 | Schob et al. |
| 6,264,635 B1 | 7/2001 | Wampler et al. |
| 6,268,675 B1 | 7/2001 | Amrhein |
| 6,276,831 B1 | 8/2001 | Takahashi et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,320,731 B1 | 11/2001 | Eaves et al. |
| 6,245,007 B1 | 12/2001 | Bedingham et al. |
| 6,458,163 B1 | 1/2002 | Slemker et al. |
| 6,351,048 B1 | 2/2002 | Schob et al. |
| 6,355,998 B1 | 3/2002 | Schob et al. |
| 6,365,996 B2 | 4/2002 | Schob |
| 6,375,607 B1 | 4/2002 | Prem |
| 6,387,037 B1 | 5/2002 | Bolling et al. |
| 6,394,769 B1 | 5/2002 | Bearnson et al. |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,522,093 B1 | 2/2003 | Hsu et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,575,717 B2 | 6/2003 | Ozaki et al. |
| 6,589,030 B2 * | 7/2003 | Ozaki ................ A61M 60/508 417/44.1 |
| 6,595,762 B2 | 7/2003 | Khanwilkar et al. |
| 6,605,032 B2 | 8/2003 | Benkowski et al. |
| 6,609,883 B2 | 8/2003 | Woodard et al. |
| 6,610,004 B2 | 8/2003 | Viole et al. |
| 6,623,420 B2 | 9/2003 | Reich et al. |
| 6,641,378 B2 | 11/2003 | Davis et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,157 B2 | 4/2004 | Goldowsky |
| 6,716,189 B1 | 4/2004 | Jarvik et al. |
| 6,732,501 B2 | 5/2004 | Yu et al. |
| 6,749,598 B1 | 6/2004 | Keren et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,846,168 B2 | 1/2005 | Davis et al. |
| 6,860,713 B2 | 1/2005 | Hoover |
| 6,884,210 B2 | 4/2005 | Nose et al. |
| 6,935,344 B1 | 8/2005 | Aboul-Hosn et al. |
| 6,926,662 B1 | 9/2005 | Aboul-Hosn et al. |
| 6,942,672 B2 | 9/2005 | Heilman et al. |
| 6,949,066 B2 | 9/2005 | Beamson et al. |
| 6,966,748 B2 | 11/2005 | Woodard et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,022,100 B1 | 4/2006 | Aboul-Hosn et al. |
| 7,048,681 B2 | 5/2006 | Tsubouchi et al. |
| 7,089,059 B1 | 8/2006 | Pless |
| 7,090,401 B2 | 8/2006 | Rahman et al. |
| 7,112,903 B1 | 9/2006 | Schob |
| 7,122,019 B1 | 10/2006 | Kesten et al. |
| 7,128,538 B2 | 10/2006 | Tsubouchi et al. |
| 7,027,875 B2 | 11/2006 | Siess et al. |
| 7,156,802 B2 | 1/2007 | Woodard et al. |
| 7,160,243 B2 | 1/2007 | Medvedev |
| 7,175,588 B2 | 2/2007 | Morello |
| 7,202,582 B2 | 4/2007 | Eckert et al. |
| 7,172,551 B2 | 6/2007 | Leasure |
| 7,241,257 B1 | 10/2007 | Ainsworth et al. |
| 7,284,956 B2 | 10/2007 | Nose et al. |
| 7,331,921 B2 | 2/2008 | Viole et al. |
| 7,335,192 B2 | 2/2008 | Keren et al. |
| 7,393,181 B2 | 7/2008 | McBride et al. |
| 7,431,688 B2 | 10/2008 | Wampler et al. |
| 7,329,236 B2 | 12/2008 | Kesten et al. |
| 7,462,019 B1 | 12/2008 | Allarie et al. |
| 7,467,930 B2 | 12/2008 | Ozaki et al. |
| 7,470,246 B2 * | 12/2008 | Mori ................ A61M 60/109 604/6.11 |
| 7,476,077 B2 | 1/2009 | Woodard et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,660,635 B1 | 2/2010 | Verness et al. |
| 7,699,586 B2 | 4/2010 | LaRose et al. |
| 7,748,964 B2 | 7/2010 | Yaegashi et al. |
| 7,731,675 B2 | 8/2010 | Aboul-Hosn et al. |
| 7,802,966 B2 | 9/2010 | Wampler et al. |
| 7,841,976 B2 | 11/2010 | McBride et al. |
| 7,862,501 B2 | 1/2011 | Woodard |
| 7,888,242 B2 | 2/2011 | Tanaka et al. |
| 7,934,909 B2 | 5/2011 | Nuesser et al. |
| 7,972,122 B2 | 7/2011 | LaRose et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,152,493 B2 | 4/2012 | LaRose et al. |
| 8,177,703 B2 | 5/2012 | Smith et al. |
| 8,226,373 B2 | 7/2012 | Yaehashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Mustafa et al. |
| 8,535,211 B2 | 9/2013 | Campbell et al. |
| 8,585,290 B2 | 11/2013 | Bauer |
| 8,686,674 B2 | 4/2014 | Bi et al. |
| 8,770,945 B2 | 7/2014 | Ozaki et al. |

(56) References Cited

U.S. PATENT DOCUMENTS

| | | | |
|---|---|---|---|
| 8,821,365 B2 * | 9/2014 | Ozaki | A61M 60/824 623/3.13 |
| 8,827,661 B2 | 9/2014 | Mori | |
| 8,652,024 B1 | 10/2014 | Yanai et al. | |
| 8,864,644 B2 | 10/2014 | Yomtov | |
| 8,870,552 B2 | 10/2014 | Ayre et al. | |
| 8,968,174 B2 | 3/2015 | Yanai et al. | |
| 9,039,595 B2 | 5/2015 | Ayre et al. | |
| 9,067,005 B2 | 6/2015 | Ozaki et al. | |
| 9,068,572 B2 | 6/2015 | Ozaki et al. | |
| 9,109,601 B2 | 8/2015 | Mori | |
| 9,132,215 B2 | 9/2015 | Ozaki et al. | |
| 9,133,854 B2 | 9/2015 | Okawa et al. | |
| 9,371,826 B2 | 6/2016 | Yanai et al. | |
| 9,381,285 B2 | 7/2016 | Ozaki et al. | |
| 9,382,908 B2 | 7/2016 | Ozaki et al. | |
| 9,410,549 B2 | 8/2016 | Ozaki et al. | |
| 9,556,873 B2 | 1/2017 | Yanai et al. | |
| 10,166,318 B2 | 1/2019 | Yu et al. | |
| 10,874,782 B2 | 12/2020 | Yu et al. | |
| 2001/0039369 A1 | 11/2001 | Terentiev | |
| 2002/0051711 A1 | 5/2002 | Ozaki | |
| 2002/0058994 A1 | 5/2002 | Hill et al. | |
| 2002/0094281 A1 | 7/2002 | Khanwilkar et al. | |
| 2002/0095210 A1 | 7/2002 | Finnegan et al. | |
| 2003/0023302 A1 | 1/2003 | Moe et al. | |
| 2003/0045772 A1 | 3/2003 | Reich et al. | |
| 2003/0072656 A1 | 4/2003 | Niwatsukino et al. | |
| 2003/0144574 A1 | 7/2003 | Heilman et al. | |
| 2003/0199727 A1 | 10/2003 | Burke | |
| 2003/0236488 A1 | 12/2003 | Novak | |
| 2003/0236490 A1 | 12/2003 | Novak | |
| 2004/0007515 A1 | 1/2004 | Geyer | |
| 2004/0015232 A1 | 1/2004 | Shu et al. | |
| 2004/0024285 A1 | 2/2004 | Muckter | |
| 2004/0030381 A1 | 2/2004 | Shu | |
| 2004/0064012 A1 | 4/2004 | Yanai | |
| 2004/0143151 A1 | 7/2004 | Mori et al. | |
| 2004/0145337 A1 | 7/2004 | Morishita | |
| 2004/0152944 A1 | 8/2004 | Medvedev et al. | |
| 2004/0171905 A1 | 9/2004 | Yu et al. | |
| 2004/0210305 A1 | 10/2004 | Shu et al. | |
| 2004/0215050 A1 | 10/2004 | Morello | |
| 2004/0263341 A1 | 12/2004 | Enzinna | |
| 2005/0004418 A1 | 1/2005 | Morello | |
| 2005/0008496 A1 | 1/2005 | Tsubouchi et al. | |
| 2005/0025630 A1 | 2/2005 | Ayre et al. | |
| 2005/0043665 A1 | 2/2005 | Vinci et al. | |
| 2005/0073273 A1 | 4/2005 | Maslov et al. | |
| 2005/0089422 A1 | 4/2005 | Ozaki et al. | |
| 2005/0131271 A1 | 6/2005 | Benkowski et al. | |
| 2005/0141887 A1 | 6/2005 | Lelkes | |
| 2005/0194851 A1 | 9/2005 | Eckert et al. | |
| 2005/0261542 A1 | 11/2005 | Abe et al. | |
| 2005/0287022 A1 | 12/2005 | Yaegashi et al. | |
| 2006/0024182 A1 | 2/2006 | Akdis et al. | |
| 2006/0055274 A1 | 3/2006 | Kim | |
| 2006/0127227 A1 | 6/2006 | Mehlhorn et al. | |
| 2007/0073393 A1 | 3/2007 | Kung et al. | |
| 2007/0078293 A1 | 4/2007 | Shambaugh | |
| 2007/0095648 A1 | 4/2007 | Wampler et al. | |
| 2007/0114961 A1 | 5/2007 | Schwarzkopf | |
| 2007/0134993 A1 | 6/2007 | Tamez et al. | |
| 2007/0189648 A1 | 8/2007 | Kita et al. | |
| 2007/0213690 A1 | 9/2007 | Phillips et al. | |
| 2007/0231135 A1 | 10/2007 | Wampler et al. | |
| 2007/0282298 A1 | 12/2007 | Mason | |
| 2007/0297923 A1 | 12/2007 | Tada | |
| 2008/0007196 A1 | 1/2008 | Tan et al. | |
| 2008/0021394 A1 | 1/2008 | La Rose et al. | |
| 2008/0030895 A1 | 2/2008 | Obara et al. | |
| 2008/0119777 A1 | 5/2008 | Vinci et al. | |
| 2008/0124231 A1 | 5/2008 | Yaegashi | |
| 2008/0183287 A1 | 7/2008 | Ayre | |
| 2008/0211439 A1 | 9/2008 | Yokota et al. | |
| 2008/0281146 A1 | 11/2008 | Morello | |
| 2009/0041595 A1 | 2/2009 | Garzaniti et al. | |
| 2009/0060743 A1 | 3/2009 | McBride et al. | |
| 2009/0074336 A1 | 3/2009 | Engesser et al. | |
| 2009/0099406 A1 | 4/2009 | Salmonsen et al. | |
| 2009/0171136 A1 | 7/2009 | Shambaugh, Jr. | |
| 2009/0257693 A1 | 10/2009 | Aiello | |
| 2009/0318834 A1 | 12/2009 | Fujiwara et al. | |
| 2010/0185280 A1 | 6/2010 | Ayre et al. | |
| 2010/0168534 A1 | 7/2010 | Matsumoto et al. | |
| 2010/0222634 A1 | 9/2010 | Poirier | |
| 2010/0234835 A1 | 9/2010 | Horikawa et al. | |
| 2010/0256440 A1 | 10/2010 | Maher | |
| 2010/0262039 A1 | 10/2010 | Fujiwara et al. | |
| 2010/0266423 A1 | 10/2010 | Gohean et al. | |
| 2010/0305692 A1 | 12/2010 | Thomas et al. | |
| 2010/0324465 A1 | 12/2010 | Vinci et al. | |
| 2011/0015732 A1 | 1/2011 | Kanebako | |
| 2011/0112354 A1 | 5/2011 | Nishimura et al. | |
| 2011/0118766 A1 | 5/2011 | Reichenbach et al. | |
| 2011/0118829 A1 | 5/2011 | Hoarau et al. | |
| 2011/0118833 A1 | 5/2011 | Reichenbach et al. | |
| 2011/0129373 A1 | 6/2011 | Mori | |
| 2011/0160519 A1 | 6/2011 | Arndt et al. | |
| 2011/0218383 A1 | 9/2011 | Broen et al. | |
| 2011/0218384 A1 | 9/2011 | Bachman et al. | |
| 2011/0218385 A1 | 9/2011 | Bolyare et al. | |
| 2011/0237978 A1 | 9/2011 | Fujiwara et al. | |
| 2011/0243759 A1 | 10/2011 | Ozaki et al. | |
| 2011/0318203 A1 | 12/2011 | Ozaki et al. | |
| 2012/0003108 A1 | 1/2012 | Ozaki et al. | |
| 2012/0016178 A1 | 1/2012 | Woodard et al. | |
| 2012/0022645 A1 | 1/2012 | Burke | |
| 2012/0035411 A1 | 2/2012 | LaRose et al. | |
| 2012/0078030 A1 | 3/2012 | Bourque | |
| 2012/0078031 A1 | 3/2012 | Burke et al. | |
| 2012/0095281 A1 | 4/2012 | Reichenbach et al. | |
| 2012/0130152 A1 | 5/2012 | Ozaki et al. | |
| 2012/0226350 A1 | 9/2012 | Ruder et al. | |
| 2012/0243759 A1 | 9/2012 | Fujisawa | |
| 2012/0245680 A1 | 9/2012 | Masuzawa et al. | |
| 2012/0245681 A1 | 9/2012 | Casas et al. | |
| 2012/0253103 A1 | 10/2012 | Jarvik | |
| 2012/0308363 A1 | 12/2012 | Ozaki et al. | |
| 2013/0030240 A1 | 1/2013 | Schima et al. | |
| 2013/0121821 A1 | 5/2013 | Ozaki et al. | |
| 2013/0158521 A1 | 6/2013 | Sobue | |
| 2013/0170970 A1 | 7/2013 | Ozaki et al. | |
| 2013/0178694 A1 | 7/2013 | Jeffery et al. | |
| 2013/0225909 A1 | 8/2013 | Dormanen et al. | |
| 2013/0243623 A1 | 9/2013 | Okawa et al. | |
| 2013/0289334 A1 | 10/2013 | Badstibner et al. | |
| 2013/0331711 A1 | 12/2013 | Mathur et al. | |
| 2014/0030122 A1 | 1/2014 | Ozaki et al. | |
| 2014/0066690 A1 | 3/2014 | Siebenhaar et al. | |
| 2014/0066691 A1 | 3/2014 | Siebenhaar | |
| 2014/0100413 A1 | 4/2014 | Casas et al. | |
| 2014/0107399 A1 | 4/2014 | Spence | |
| 2014/0142367 A1 | 5/2014 | Ayre et al. | |
| 2014/0155682 A1 | 6/2014 | Jeffery et al. | |
| 2014/0200389 A1 | 7/2014 | Yanai et al. | |
| 2014/0205467 A1 | 7/2014 | Yanai et al. | |
| 2014/0241904 A1 * | 8/2014 | Yanai | A61M 60/422 417/420 |
| 2014/0275721 A1 | 9/2014 | Yanai et al. | |
| 2014/0275727 A1 | 9/2014 | Bonde et al. | |
| 2014/0296615 A1 | 10/2014 | Franano | |
| 2014/0309481 A1 | 10/2014 | Medvedev et al. | |
| 2014/0314597 A1 | 10/2014 | Allaire et al. | |
| 2014/0323796 A1 | 10/2014 | Medvedev et al. | |
| 2014/0343352 A1 | 11/2014 | Ardt et al. | |
| 2015/0017030 A1 | 1/2015 | Ozaki | |
| 2015/0023803 A1 | 1/2015 | Fritz et al. | |
| 2015/0078936 A1 | 3/2015 | Mori | |
| 2015/0306290 A1 | 10/2015 | Rosenberg et al. | |
| 2015/0367048 A1 | 12/2015 | Brown et al. | |
| 2015/0374892 A1 | 12/2015 | Yanai et al. | |
| 2016/0058929 A1 | 3/2016 | Medvedev et al. | |
| 2016/0058930 A1 | 3/2016 | Medvedev et al. | |

(56) References Cited

U.S. PATENT DOCUMENTS

| | | |
|---|---|---|
| 2016/0228628 A1 | 8/2016 | Medvedev et al. |
| 2016/0235898 A1 | 8/2016 | Yanai et al. |
| 2016/0235900 A1 | 8/2016 | Yanai et al. |
| 2016/0281720 A1 | 9/2016 | Yanai et al. |

FOREIGN PATENT DOCUMENTS

| | | |
|---|---|---|
| CN | 102239334 A | 11/2011 |
| CN | 102341600 A | 2/2012 |
| EP | 971212 A | 1/2000 |
| EP | 1113117 A2 | 7/2001 |
| EP | 1327455 A | 7/2003 |
| EP | 1430919 A1 | 6/2004 |
| EP | 1495773 A2 | 1/2005 |
| EP | 1598087 A2 | 3/2005 |
| EP | 1526286 A1 | 4/2005 |
| EP | 1495773 A3 | 11/2006 |
| EP | 1495773 B1 | 2/2009 |
| EP | 2292282 A1 | 3/2011 |
| EP | 2298375 A1 | 3/2011 |
| EP | 2372160 A1 | 10/2011 |
| EP | 2405140 A1 | 1/2012 |
| EP | 2405141 A1 | 1/2012 |
| EP | 2461465 A1 | 6/2012 |
| EP | 2538086 A1 | 12/2012 |
| EP | 2554191 A1 | 2/2013 |
| EP | 2594799 A1 | 5/2013 |
| EP | 2618001 A1 | 7/2013 |
| EP | 2693609 A1 | 2/2014 |
| EP | 2948202 A1 | 12/2015 |
| EP | 2961987 A1 | 1/2016 |
| EP | 3013385 A2 | 5/2016 |
| EP | 2945662 B1 | 4/2018 |
| JP | 58-009535 | 1/1983 |
| JP | 61-293146 | 12/1986 |
| JP | H02-007780 U | 1/1990 |
| JP | H02-033590 U | 3/1990 |
| JP | 04-091396 A | 3/1992 |
| JP | 04-148094 A | 5/1992 |
| JP | 05-021197 U | 3/1993 |
| JP | 06-014538 U | 2/1994 |
| JP | 06-053790 U | 7/1994 |
| JP | 2006-070476 | 9/1994 |
| JP | 2006-245455 | 9/1994 |
| JP | 07-014220 U | 3/1995 |
| JP | 07-042869 U | 8/1995 |
| JP | 07-509156 A | 10/1995 |
| JP | 09-122228 A | 5/1997 |
| JP | 10-331841 A | 12/1998 |
| JP | 11-244377 A | 9/1999 |
| JP | 2001-309628 | 11/2001 |
| JP | 2003-135592 A | 5/2003 |
| JP | 2004-166401 A | 6/2004 |
| JP | 2004-209240 A | 7/2004 |
| JP | 2004-332566 A | 11/2004 |
| JP | 2004-346925 A | 12/2004 |
| JP | 2005-094955 | 4/2005 |
| JP | 2005-127222 A | 5/2005 |
| JP | 2005-245138 | 9/2005 |
| JP | 2005-270345 A | 10/2005 |
| JP | 2005-270415 A | 10/2005 |
| JP | 2005-287599 A | 10/2005 |
| JP | 2006-167173 A | 6/2006 |
| JP | 2007-002885 A | 1/2007 |
| JP | 2007-043821 | 2/2007 |
| JP | 2007-089972 A | 4/2007 |
| JP | 2007-089974 | 4/2007 |
| JP | 2007-215292 | 8/2007 |
| JP | 2007-247489 | 9/2007 |
| JP | 2008-011611 | 1/2008 |
| JP | 2008-104278 | 5/2008 |
| JP | 2008-132131 | 6/2008 |
| JP | 2008-99453 | 8/2008 |
| JP | 2008-193838 | 8/2008 |
| JP | 2008-297997 A | 12/2008 |
| JP | 2008-301634 | 12/2008 |
| JP | 2006-254619 | 9/2009 |
| JP | 2010-133381 A | 6/2010 |
| JP | 2010-136863 A | 6/2010 |
| JP | 2010-203398 A | 9/2010 |
| JP | 2010-209691 A | 9/2010 |
| JP | 2011-169166 A | 9/2011 |
| JP | 2012-021413 | 2/2012 |
| JP | 2012-062790 A | 3/2012 |
| JP | 5171953 B2 | 3/2013 |
| JP | 5572832 B2 | 8/2014 |
| JP | 5656835 B2 | 1/2015 |
| WO | 1993-07388 A1 | 4/1993 |
| WO | 94-14226 | 6/1994 |
| WO | 1996-31934 | 10/1996 |
| WO | 1997-42413 A1 | 11/1997 |
| WO | 2000-64509 A1 | 11/2000 |
| WO | 2004-098677 A1 | 11/2004 |
| WO | 2005-011087 A1 | 2/2005 |
| WO | 2005-028000 A1 | 3/2005 |
| WO | 2005-034312 A2 | 4/2005 |
| WO | 2009-157408 A1 | 12/2009 |
| WO | 2010-067682 A1 | 6/2010 |
| WO | 2010-101082 A1 | 9/2010 |
| WO | 2010-101107 A1 | 9/2010 |
| WO | 2011-013483 A1 | 2/2011 |
| WO | 2012-036059 A1 | 3/2012 |
| WO | 2012-040544 A1 | 3/2012 |
| WO | 2012-047550 A1 | 4/2012 |
| WO | 2012-132850 A1 | 10/2012 |
| WO | 2014-113533 A1 | 7/2014 |
| WO | 2014-116676 A1 | 7/2014 |
| WO | 2014-133942 A1 | 9/2014 |
| WO | 2014-179271 A2 | 11/2014 |
| WO | 2016-033131 A1 | 3/2016 |
| WO | 2016-033133 A1 | 3/2016 |
| WO | 2016-130846 A1 | 8/2016 |
| WO | 2016-130944 A1 | 8/2016 |
| WO | 2016-130955 A1 | 8/2016 |
| WO | 2016-130989 A1 | 8/2016 |

OTHER PUBLICATIONS

Asama, J., et al.,"A New Design for a Compact Centrifugal Blood Pump with a Magnetically Levitated Rotor", Asaio Jopurnal, vol. 50, No. 6, Nov. 1, 2004 (Nov. 1, 2004), pp. 550-556.

Asama, et al., "Suspension Performance of a Two-Axis Actively Regulated Consequent-Pole Bearingless Motor," IEEE Transactions on Energy Conversion, vol. 28, No. 4, Dec. 2013, 8 pages.

European Search report Issued in European Patent Application No. 10748702.7, dated Apr. 2, 2013.

Extended European Search Report issued in European Patent Application No. EP 10748677.1, dated Nov. 19, 2012.

Extended European Search Report issued in European Patent Application No. EP 11825062.0, dated Jun. 18, 2015, all pages.

Extended European Search Report issued in European Patent Application No. EP 11806627.3, dated Oct. 8, 2014, all pages.

Extended European Search Report dated Apr. 2, 2015 in European Patent Application No. EP 09770118.9 filed Jun. 22, 2009, all pages.

International Search Report and written opinion dated Jul. 14, 2009 for International Patent Application No. PCT-JP2009-061318, all pages.

International Search Report and Written Opinion dated Apr. 12, 2011 in International Patent Application No. PCT/JP2011/050925, all pages.

International Search Report and Written Opinion dated Apr. 12, 2011 in International Patent Application No. PCT/JP2011/054134, all pages.

International Search Report and Written Opinion dated Sep. 13, 2011 in International Patent Application No. PCT/JP2011/064768, all pages.

International Search Report and Written Opinion dated Dec. 13, 2011 in International Patent Application No. PCT/JP2011/070450, all pages.

(56) References Cited

OTHER PUBLICATIONS

International Search Report and Written Opinion dated Feb. 19, 2014 in International Patent Application No. PCT/US2014/012448, all pages.
International Search Report and Written Opinion dated May 9, 2014 in International Patent Application No. PCT/US2014/011786, all pages.
International Search Report and Written Opinion dated May 9, 2014 in International Patent Application No. PCT/US2014/012502, all pages.
International Search Report and Written Opinion dated May 14, 2014 in International Patent Application No. PCT/US2014/012511, all pages.
International Search Report and Written Opinion dated Jun. 16, 2014 in International Patent Application No. PCT/US2014/017932, all pages.
International Preliminary Report on Patentability dated Aug. 6, 2015 for International Patent Application No. PCT/US2014/012511 filed on Jan. 22, 2014, all pages.
International Preliminary Report on Patentability dated Aug. 6, 2015 for International Patent Application No. PCT/US2014/012502 filed on Jan. 22, 2014, all pages.
International Preliminary Report on Patentability dated Feb. 25, 2016 for International Patent Application No. PCT/US2014/035798 filed on Apr. 29, 2014, all pages.
Kosaka, et al., "Operating Point Control System for a Continuous Flow Artificial Heart: In Vitro Study," ASAIO Journal 2003, all pages.
Neethu, S., et al., "Novel design, optimization and realization of axial flux motor for implantable blood pump", Power Electronics, Drives and Energy Systems (PEDES) & 2010 Power Indian, 2010 Joint International Conference on, IEEE, Dec. 20, 2010 (Dec. 20, 2010), pp. 1-6.
Sandtner, J., et al., "Electrodynamic Passive Magnetic Bearing with Planar Halbach Arrays", Aug. 6, 2004 (Aug. 6, 2004), retrieved from the internet: <http:--www.silphenix.ch-lexington.pdf>, all pages.
Supplementary European Search Report issued in European Application No. 09831788.6, dated Jan. 7, 2013, all pages.
Terumo Heart, Inc., "Handled With Care—Significantly Reduce the Risk of Cell Damage," Terumo brochure, Apr. 2010, 2 pages.
Yamazaki, et al., "Development of a Miniature Intraventricular Axial Flow Blood Pump," ASAIO Journal, 1993, 7 pages.
European office action dated Jan. 27, 2016 for EP 10804230.0, all pages.
Extended European Search Report dated Feb. 4, 2016 in European Patent Application No. EP 12764433.4, filed Mar. 12, 2012, all pages.
International Preliminary Report on Patentability dated Jul. 30, 2015 for International Patent Application No. PCT/US2014/011786, filed on Jan. 16, 2014, all pages.
International Preliminary Report on Patentability dated Sep. 11, 2015 for International Patent Application No. PCT/US2014/017932, filed on Feb. 24, 2014, all pages.
International Search Report and Written Opinion dated Feb. 11, 2016 in International Patent Application No. PCT/US2014/035798, all pages.
International Search Report and Written Opinion of PCT/US2016/017611, dated May 16, 2016, all pages.
International Search Report and Written Opinion dated May 16, 2016 in International Patent Application No. PCT/US2016/017791, all pages.
Japanese office action dated Dec. 11, 2015 JP 2013-507344, all pages.
International Search Report and Written Opinion dated Jun. 7, 2016 in International Patent Application No. PCT/US2016/017812, all pages.
International Search Report and Written Opinion dated Jun. 8, 2016 in International Patent Application No. PCT/US2016/017864, all pages.
Notice of Decision to Grant for JP 2013-507344 dated Jun. 15, 2016, all pages.
European office action dated Jul. 22, 2016 for European Patent Application No. EP 09770118.9, all pages.
European office action dated Sep. 8, 2016 for EP 14741174, all pages.
Extended European Search Report for EP 14743371.8 dated Sep. 29, 2016, all pages.
International Search Report and Written Opinion dated Oct. 27, 2015 in International Patent Application No. PCT/US2015/046844, all pages.
International Search Report and Written Opinion dated Oct. 27, 2015 in International Patent Application No. PCTUS2015/046846, all pages.
European office action dated Oct. 31, 2016 for EP 10804230.0, all pages.
European Office Action dated Jul. 19, 2016 in European Patent Application No. 11825062, all pages.
Gieras, et al., "Advancements in Electric Machines", Nov. 14, 2008, pp. 43-48.
International Search Report and Written Opinion dated Feb. 24, 2017 in International Patent Application No. PCT/US2016/062284, all pages.

* cited by examiner

SYSTEM AND METHOD FOR CONTROLLING THE POSITION OF A LEVITATED ROTOR

CROSS-REFERENCE TO RELATED APPLICATIONS

This application is a continuation of U.S. patent application Ser. No. 16/218,791, filed Dec. 13, 2018, and entitled "SYSTEM AND METHOD FOR CONTROLLING THE POSITION OF A LEVITATED ROTOR," which is a continuation of U.S. patent application Ser. No. 15/042,431, filed Feb. 12, 2016, now U.S. Pat. No. 10,166,318 issued Jan. 1, 2019, and entitled "SYSTEM AND METHOD FOR CONTROLLING THE POSITION OF A LEVITATED ROTOR," the entire disclosures of which are hereby incorporated by reference, for all purposes, as if fully set forth herein.

U.S. patent application Ser. No. 15/042,431, now U.S. Pat. No. 10,166,318 issued Jan. 1, 2019, claims priority to and the benefit of U.S. Provisional Application No. 62/115,603, filed Feb. 12, 2015, and entitled "SYSTEM AND METHOD FOR CONTROLLING THE POSITION OF A LEVITATED ROTOR," the entire disclosure of which is hereby incorporated by reference, for all purposes, as if fully set forth herein.

U.S. patent application Ser. No. 15/042,431, now U.S. Pat. No. 10,166,318 issued Jan. 1, 2019, claims priority to and the benefit of U.S. Provisional Application No. 62/115,324, filed Feb. 12, 2015, and entitled "SYSTEM AND METHOD FOR CONTROLLING THE POSITION OF A LEVITATED ROTOR," the entire disclosure of which is hereby incorporated by reference, for all purposes, as if fully set forth herein.

BACKGROUND OF THE INVENTION

The present invention relates in general to rotary devices, and more specifically, to improved pumping devices and methods for their control.

One exemplary type of rotary machine is a centrifugal pumping device or mechanical circulatory assist device for treating patients with heart failure. Many types of circulatory assist devices are available for either short term or long term support for patients having cardiovascular disease. For example, a heart pump system known as a left ventricular assist device (LVAD) can provide long term patient support with an implantable pump associated with an externally-worn pump control unit and batteries. The LVAD improves circulation throughout the body by assisting the left side of the heart in pumping blood. Examples of LVAD systems are the DuraHeart® LVAS system made by Terumo Heart, Inc. of Ann Arbor, Mich. and the HeartMate II™ and HeartMate III™ systems made by Thoratec Corporation of Pleasanton, Calif. These systems typically employ a centrifugal pump with a magnetically levitated impeller to pump blood from the left ventricle to the aorta. The impeller is formed as the rotor of the electric motor and rotated by the rotating magnetic field from a multiphase stator such as a brushless DC motor (BLDC). The impeller is rotated to provide sufficient blood flow through the pump to the patient's systemic circulation.

Early LVAD systems utilized mechanical bearings such as ball-and-cup bearings. More recent LVADs employ non-contact bearings which levitate the impeller using hydrodynamic and/or magnetic forces. In one example, the impeller is levitated by the combination of hydrodynamic and passive magnetic forces.

There is a trend for making centrifugal blood pumps used as the mechanical circulatory support devices more miniaturized to treat a broader patient population, more reliable, and with improved outcomes. To follow this trend, contactless impeller suspension technology has been developed in several pump designs. The principle of this technology is to levitate the pump impeller using one or a combination of forces from electromagnets, hydrodynamics, and permanent magnets. In the meanwhile, the pump should be hemocompatible to minimize the blood cell damage and blood clot formation. To that end, the bearing gap between the levitated impeller and the pump housing becomes an important factor. A small gap may lead to the high probability of the thrombus formation in the bearing or to elevated hemolysis due to excessive shear stress. Likewise, a large gap can compromise the hydrodynamic bearing performance and the pump efficiency.

One pump design utilizing active magnetic bearings achieves the desired bearing gap by levitating the impeller using magnetic fields generated by electromagnetic coils. However, in such a design there is the need for a separate bearing control system that includes the position sensors and electromagnetic coils to control the impeller position. Another pump design levitates the impeller using hydrodynamic thrust bearings combined with passive magnetic bearings. However, such a design usually requires a small bearing gap to provide sufficient hydrodynamic bearing stiffness to maintain impeller levitation and prevent contacts between impeller and the pump housing. Such a small gap may result in an insufficient washout and vulnerability to blood clotting thus compromising hemocompatibility.

Therefore, a solution is needed to enhance the bearing gap to achieve adequate washout without increasing the complexity of the pump mechanical design and reducing the pump efficiency.

There is a need for a pump that includes an integrated control method for controlling the impeller position to enhance the bearing gap without increasing the complexity of the pump mechanical design and reducing the pump efficiency.

There is the need for a blood pump designed to maintain a centered position of the impeller to limit hemolysis and thrombosis without needing active control of the stationary levitating magnetic field.

There is a need for pumps which overcomes the above and other disadvantages of known designs.

BRIEF SUMMARY OF THE INVENTION

In summary, various aspects of the present invention are directed to a rotary machine including a rotor within a housing and having a rotor magnetic structure; a stator on a side of the housing for generating a rotating magnetic field for applying a torque to the rotor magnetic structure; a commutator circuit for providing a plurality of phase voltages to the stator; and a controller for rotating the rotor using the commutator circuit and a vector control algorithm. In one embodiment the controller is configured to adjust the phase voltages to modify an attractive force of the stator on the rotor magnetic structure to translate the rotor.

In various embodiments, the machine further includes a sensing circuit for determining a position of the rotor. The controller may be configured to calculate successive commanded values for the phase voltages in response to determined phase currents from the sensing circuit and a variable commutation angle. The angle for calculating the commanded values may be determined in response to a phase current characteristic and a rotational speed of the rotor.

In various embodiments, the rotor is levitated by a substantially constant passive magnetic field.

In various embodiments, the controller is configured to move the rotor from a first balanced position to a second balanced position.

Various aspects of the invention are directed to a rotary machine including a rotor within a housing and having a rotor magnetic structure; a bearing mechanism for suspending the rotor in the housing in a balanced, non-contact manner; motor coils on a side of the housing for generating a magnetic field to apply a torque on the rotor magnetic structure; at least a first sensing circuit for determining a rotational and axial position of the rotor; a controller for rotating the rotor using the motor coils; and an impeller position control mechanism for adjusting a position of the impeller in the housing.

In various embodiments, the bearing mechanism comprises one of a hydrodynamic bearing, magnetic bearing, or combination of the same. In various embodiments, the modification of the attractive force on the rotor magnetic structure by the controller causes the rotor to move from a first balanced position to a second balanced position. The sensing circuit may include a plurality of position sensors for detecting the axial and rotational position of the rotor. The plurality of position sensors may include Hall-effect sensors. The plurality of position sensors may include optical sensors. In various embodiments, the rotor magnetic structure includes a plurality of magnetic members.

In various embodiments, the rotary machine is a pump. In various embodiments, the rotary machine is a blood pump. In various embodiments, the rotor is formed as an impeller.

Various aspects of the invention are directed to a method of operating the rotary machine described in any of the paragraphs above.

Various aspects of the invention are directed to a method of operating a centrifugal pump including a stator having windings and an impeller rotating in a non-contact manner within a pump housing, the impeller including a magnetic structure, the method includes applying a first levitating force on the impeller during rotation; and using electromagnetic windings, controlling the position of the impeller in the pump housing axially and rotationally.

In various embodiments, the first levitating force comprises a passive magnetic attractive force. The at least second levitating force may include an active magnetic force created by electromagnetic coils. The coils may be driven by vector control.

Various aspects of the invention are directed to a method of operating a centrifugal pump including a stator having windings and an impeller rotating in a non-contact manner within a pump housing, the impeller including a magnetic structure, the method including applying a first levitating force on the impeller during rotation; and using electromagnetic windings, controlling the position of the impeller in the pump housing axially and rotationally.

In various embodiments, the stator windings form the electromagnetic windings for controlling the impeller position. In various embodiments, the rotation of the impeller is controlled by interaction between the magnetic structure in the impeller and AC currents in the motor stator windings. In various embodiments, the axial position of the impeller is controlled by interaction between the magnetic structure in the impeller and DC currents in the motor stator windings.

In various embodiments, the method includes using the electromagnetic windings to move the impeller axially from a first predetermined position to a second predetermined within the pump housing.

Various aspects of the invention are directed to a system, method, or computer-program product as described herein and/or shown in any of the drawings.

The systems and methods of the present invention have other features and advantages which will be apparent from or are set forth in more detail in the accompanying drawings, which are incorporated in and form a part of this specification, and the following Detailed Description of the Invention, which together serve to explain the principles of the present invention.

DETAILED DESCRIPTION OF THE INVENTION

Figure 1:
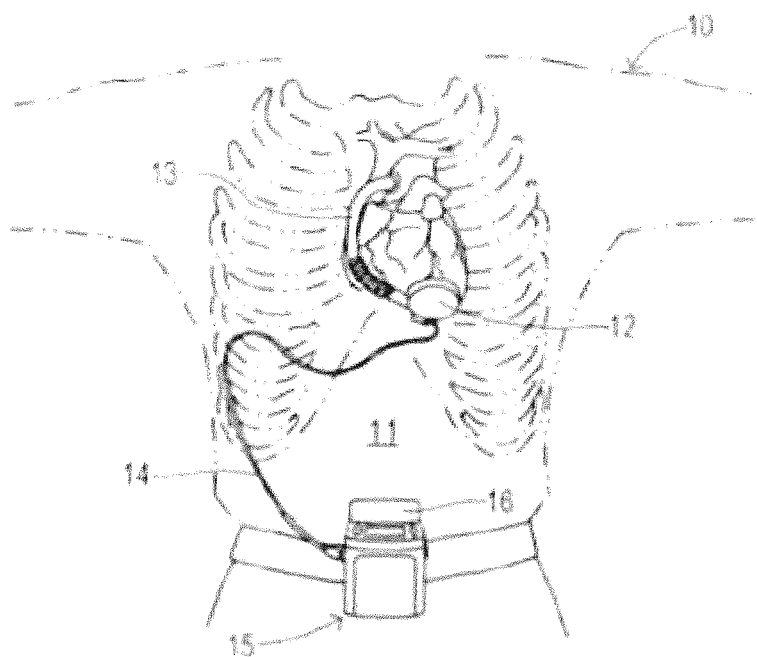
FIG. 1 is a diagram of an implantable pump as one example of a rotary machine employing the present invention.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

For convenience in explanation and accurate definition in the appended claims, the terms "up" or "upper", "down" or "lower", "inside" and "outside" are used to describe features of the present invention with reference to the positions of such features as displayed in the figures.

In many respects the modifications of the various figures resemble those of preceding modifications and the same reference numerals followed by subscripts "a", "b", "c", and "d" designate corresponding parts.

As used herein, "gap" generally refers to the secondary flow gaps around the impeller as would be understood by one of skill in the art. The primary flow is through the impeller blade regions. The secondary flow gaps are the other areas of fluid, generally around the impeller. In some respects, the secondary flow gaps are between the impeller and the housing wall and define the hydrodynamic bearing.

The term "machine-readable medium" includes, but is not limited to portable or fixed storage devices, optical storage devices, wireless channels and various other mediums capable of storing, containing or carrying instructions and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. One or more processors may perform the necessary tasks.

Although aspects of the invention will be described with reference to a blood pump, one will appreciate that the invention can be applied to various rotary machines and other types of pumps. The mechanisms and methods of the invention will be described in relation to blood pumps and in particular the ability to adjust the impeller operating position to address performance, such as the attendant risks for thrombus and hemolysis when pumping blood. One will appreciate from the description herein that the invention can be applied broadly to other pumps, rotary machines, and induction motors.

Aspects of the invention enable to the ability to enhance or control the bearing gap. One might wish to increase the bearing gap to adjust the washout rate, lubricate the bearing surfaces, or remove materials (particulates, thrombus, etc.) from the bearing gap. Another use of the invention may be to increase pump efficiency. As is known in the art, the motor efficiency increases as the impeller magnet moves closer to the motor drive coils. Another use of the invention may be to correct impeller malpositioning due to bulk forces or external forces (e.g. bumps or movements of the patient's body). These and other advantages can be achieved without the need for complex control systems in accordance with the invention.

In one embodiment, an electromagnetic force control method is used to change the impeller position and enhance the effective gap between the impeller and the blood chamber. The technique uses the same pump motor stator coils adjust the impeller position as is used to apply a torque to the impeller. No additional control subsystems and components are necessary.

Turning now to the drawings, wherein like components are designated by like reference numerals throughout the various figures, attention is directed to FIG. 1 which depicts an exemplary pump implanted in a heart failure patient.

A typical cardiac assist system includes a pumping unit, drive electronics, microprocessor control unit, and an energy source such as rechargeable batteries and/or an AC power conditioning circuit. The system is implanted during a surgical procedure in which a centrifugal pump is placed in the patient's chest. An inflow conduit is pierced into the left ventricle to supply blood to the pump. One end of an outflow conduit is mechanically fitted to the pump outlet and the other end is surgically attached to the patient's aorta by anastomosis. A percutaneous cable connects to the pump, exits the patient through an incision, and connects to the external control unit.

Various aspects of the implantable pump are similar to those shown and described in U.S. Pat. Nos. 4,528,485; 4,857,781; 5,229,693; 5,588,812; 5,708,346; 5,917,297; 6,100,618; 6,222,290; 6,249,067; 6,268,675; 6,355,998; 6,351,048; 6,365,996; 6,522,093; 7,972,122; 8,686,674; 8,770,945; U.S. Pub. No. 2014/0205467; 2012/0095281; and U.S. patent application Ser. No. 15/041,987, the entire contents of which patents and publications are incorporated herein by this reference for all purposes.

The exemplary system utilizes an implantable pump with contactless bearings for supporting the impeller. Contactless bearings (i.e., levitation) provide a number of potential benefits. Because they reduce rotational friction, theoretically they improve motor efficiency and reduce the risk of introducing particulates into the fluid. In one example, the impeller employs upper and lower plates having magnetic materials (the terminology of upper and lower being arbitrary since the pump can be operated in any orientation). A stationary magnetic field from the upper side of the pump housing attracts the upper plate and a rotating magnetic field from the lower side of the pump housing attracts the lower plate. The forces cooperate so that the impeller rotates at a levitated position within the pumping chamber. Features (not shown) may also be formed in the walls of the pumping chamber to produce a hydrodynamic bearing wherein forces from the circulating fluid also tend to center the impeller. Hydrodynamic pressure grooves adapted to provide such a hydrodynamic bearing are shown in U.S. Pat. No. 7,470,246, issued Dec. 30, 2008, titled "Centrifugal Blood Pump Apparatus," which is incorporated herein for all purposes by reference.

The exemplary impeller has an optimal location within the pumping chamber with a predetermined spacing from the chamber walls on each side. Maintaining a proper spacing limits the shear stress and the flow stasis of the pump. A high shear stress can cause hemolysis of the blood (i.e., damage to cells). Flow stasis can cause thrombosis (i.e., blood clotting).

With continued reference to FIG. 1, a patient is shown in fragmentary front elevational view. Surgically implanted either into the patient's abdominal cavity or pericardium 11 is the pumping unit 12 of a ventricular assist device. An inflow conduit (on the hidden side of unit 12) pierces the apex of the heart to convey blood from the patient's left ventricle into pumping unit 12. An outflow conduit 13 conveys blood from pumping unit 12 to the patient's ascending aorta. A percutaneous power cable 14 extends from pumping unit 12 outwardly of the patient's body via an incision to a compact control unit 15 worn by patient 10. Control unit 15 is powered by a main battery pack 16 and/or an external AC power supply, and an internal backup battery. Control unit 15 includes a commutator circuit for driving a motor within pumping unit 12.

In various embodiments, the commutator circuit and/or various electronics may be on the implanted side of the system. For example, various electronics may be positioned on-board the pump or in a separate hermetically sealed housing. Among the potential advantages of implanting electronics is the ability to control the pump even when communication is lost with the control unit 15 outside the body.

Figure 2:
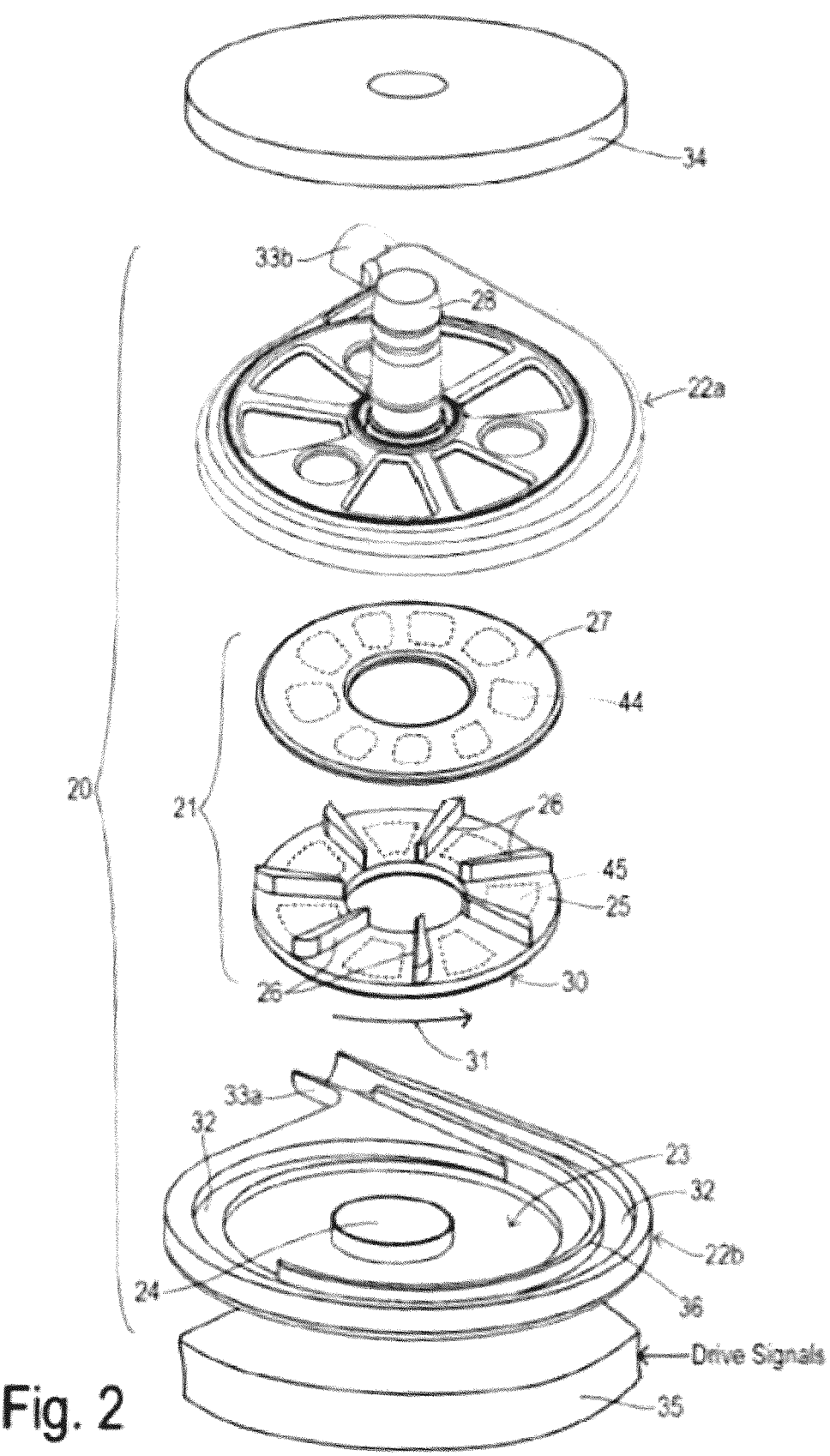
FIG. 2 is an exploded, perspective view of the exemplary centrifugal pump of FIG. 1.

FIG. 2 shows exemplary centrifugal pump unit 20 used in the system of FIG. 1. The pump unit 20 includes an impeller 21 and a pump housing having upper and lower halves 22a and 22b. Impeller 21 is disposed within a pumping chamber 23 over a hub 24. Impeller 21 includes a first plate or disc 25 and a second plate or disc 27 sandwiched over a plurality of vanes 26. Second disc 27 includes a plurality of embedded magnet segments 44 for interacting with a levitating magnetic field created by levitation magnet structure 34 disposed against housing 22a. For achieving a small size, magnet structure 34 may comprise one or more permanent magnet segments providing a symmetrical, static levitation magnetic field around a 3600 circumference. First disc 25 also contains embedded magnet segments 45 for magnetically coupling with a magnetic field from a stator assembly 35 disposed against housing 22b. Housing 22a includes an inlet 28 for receiving blood from a patient's ventricle and distributing it to vanes 26. Impeller 21 is preferably circular and has an outer circumferential edge 30. By rotatably driving impeller 21 in a pumping direction 31, the blood received at an inner edge of impeller 21 is carried to outer circumferential 30 and enters a volute region 32 within pumping chamber 23 at an increased pressure. The pressurized blood flows out from an outlet 33 formed by housing features 33a and 33b. A flow-dividing guide wall 36 may be provided within volute region 32 to help stabilize the overall flow and the forces acting on impeller 21.

Figure 3:
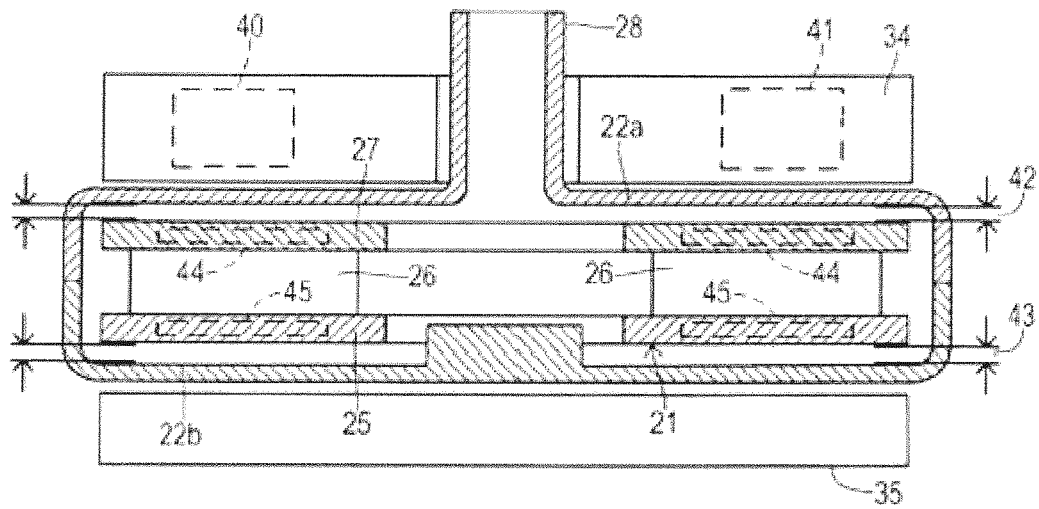
FIG. 3 is a cross-sectional view of the exemplary pump of FIG. 1, illustrating the impeller levitated at a first balanced position generally centered within the pumping chamber in accordance with aspects of the invention.

FIG. 3 shows an exemplary pump 10 similar to the pump shown in FIG. 2. FIG. 3 shows impeller 21 located in a balanced position. The balanced position sometimes refers to the position the impeller naturally stabilizes or finds equilibrium during operation. In the exemplary embodiment, the balanced position is at or near the center of the pump chamber. In the balanced position, the forces acting on the impeller are generally balanced to stabilize the impeller. As one will understand from the description above that the hydrodynamic forces on the impeller will change as the rotational speed of the impeller changes. In turn, the magnetic attractive forces on the impeller will change as the impeller moves closer to or away from the magnet structure 34 and stator assembly 35. Accordingly, the impeller generally finds a new balanced position as the rotational speed changes.

As will be described below, however, aspects of the invention are directed to moving the impeller or changing the balanced position for each given rotational speed. For example, the impeller position control mechanisms to be described facilitate moving the impeller axially (up or down) without changing the rotational speed and all other. This has the effect of enabling movement of the impeller independent of rotor speed. An advantage of this technique is that rotor speed can be determined in normal course (e.g. by a physician based on the patient's physiological needs) without concern for changing the impeller position. Conversely, the impeller position can be changed without affecting pumping throughput.

FIG. 3 shows impeller 21 located at or near a centered position wherein disc 27 is spaced from housing 22A by a gap 42 and impeller disc 25 is spaced from housing 22B by a gap 43. In the exemplary embodiment, the center position is chosen as the balanced or balanced position to ensure substantially uniform flow through gaps 42 and 43. During pump operation, the balanced position is maintained by the interaction of (a) attractive magnetic forces between permanent magnets 40 and 41 in levitation magnet structure 34 with imbedded magnetic material 44 within impeller disc 27, (b) attractive magnetic forces between stator assembly 35 and embedded magnet material 45 in impeller disc 25, and (c) hydrodynamic bearing forces exerted by the circulating fluid which may be increased by forming hydrodynamic pressure grooves in housing 22 (not shown). By using permanent magnets in structure 34 a compact shape is realized and potential failures associated with the complexities of implementing active levitation magnet control are avoided. To properly balance impeller 21 at the centered position, however, and because other forces acting on impeller 21 are not constant, an active positioning control may be desired. In particular, the hydrodynamic forces acting on impeller 21 vary according to the rotational speed of impeller 21. Furthermore, the attractive force applied to impeller 21 by stator assembly 35 depends on the magnitude of the magnetic field and the angle by which the magnetic field leads the impellers magnetic field position.

The structures and methods for controlling the motor will now be described with references to FIGS. 4 to 6.

Figure 4:
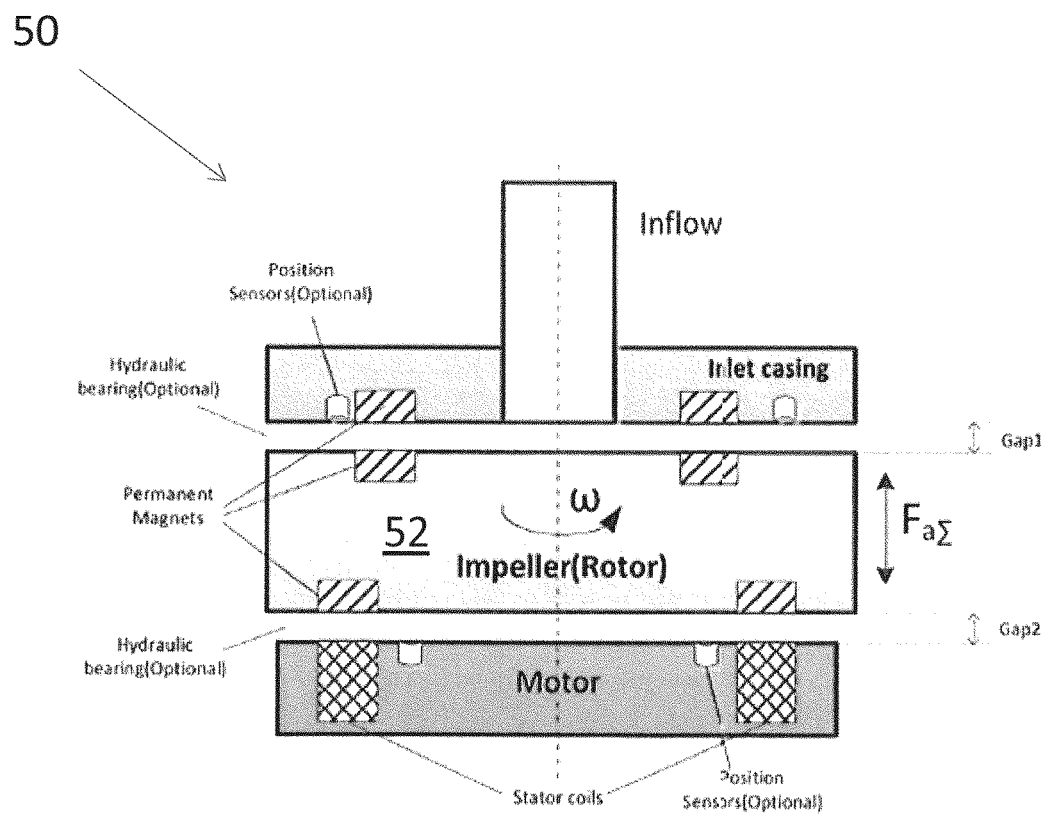
FIG. 4 is a schematic view of the exemplary pump of FIG. 1, illustrating the impeller levitated eccentrically in the pump chamber by the main bearing components.

FIG. 4 shows the main structure of an exemplary centrifugal pump 50 similar to that shown in FIG. 3. It is understood that other pump configurations may be employed, including various combinations of permanent magnets, motor stator windings, and hydrodynamic bearings. In the exemplary embodiment, the rotor is formed as an impeller and driven by a motor. The impeller is also levitated by the combined force $F_{a\Sigma}$, which can be expressed as the following equation:

$$F_{a\Sigma}=F_{hdb}+F_{pm}+F_{em}$$

Where, $F_{a\Sigma}$ is the combined force to levitate the impeller $F_{hdb}$ is the combination of hydrodynamic forces from the inlet side bearing, the motor side bearing, or both $F_{pm}$ is the combination of permanent magnet attraction forces $F_{em}$ is the magnetic attraction force generated from the motor When the impeller is stabilized, $F_{a\Sigma}$ should be equal to zero. Usually $F_{em}$ can be controlled through the electronic system to adjust the impeller position since all the others are the fixed configurations as the passive mode. Therefore, the basic design concept of this invention is to apply the motor vector control (FOC) to control the force $F_{em}$ so that the impeller position can be adjusted while rotating only using one set of motor coil and drive system. In such way, there is no additional cost in the pump structure.

Figure 5:
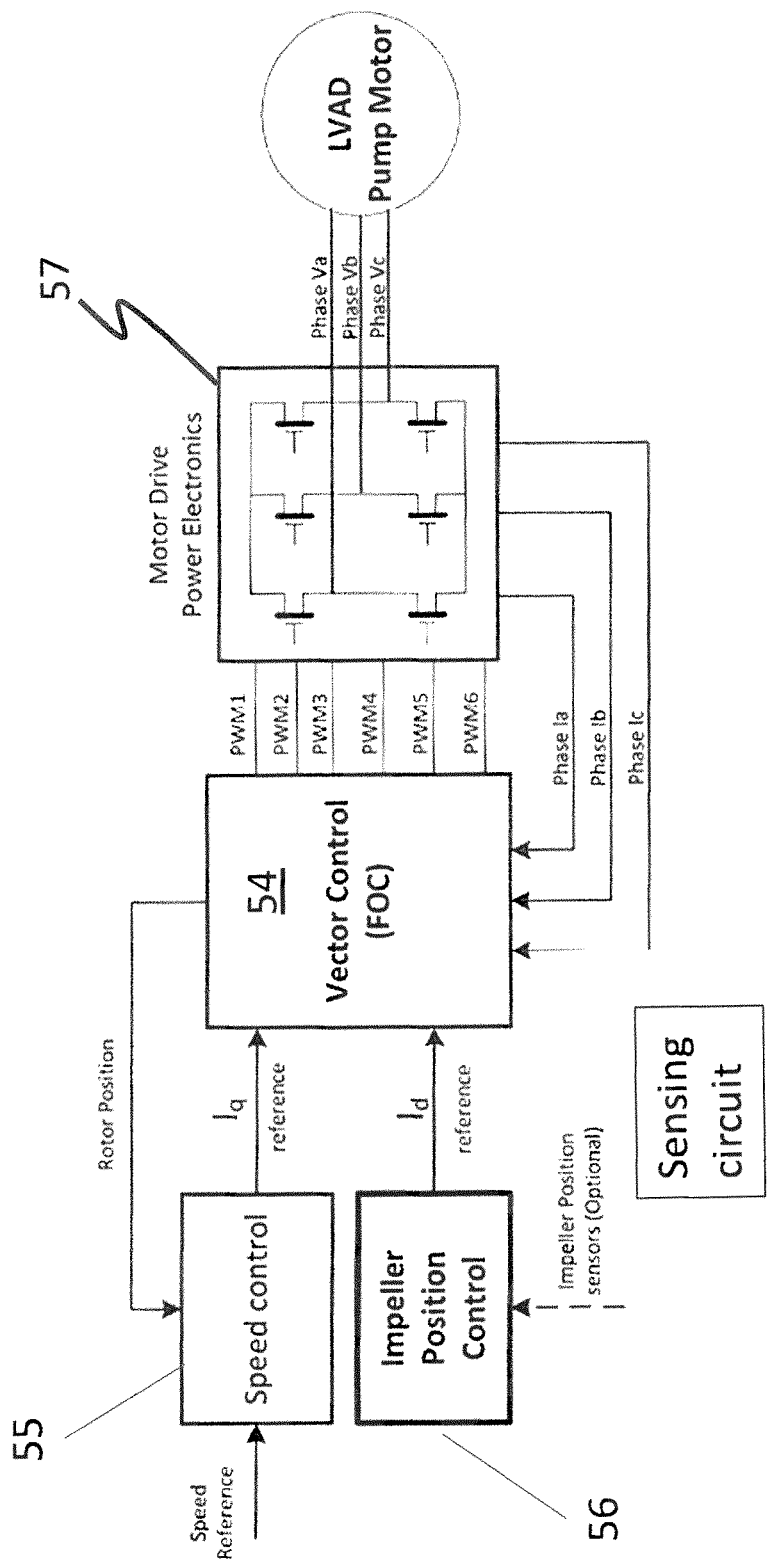
FIG. 5 is a block diagram of a pump control system in accordance with the invention.
Figure 6:
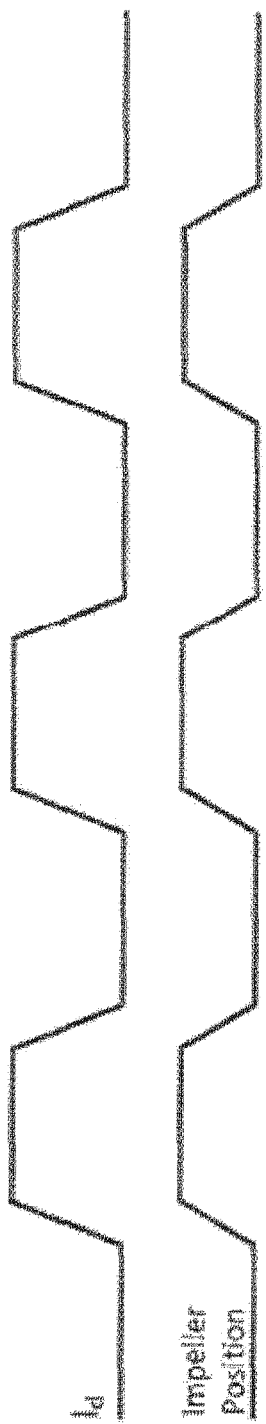
FIG. 6 is a line chart depicting the method of controlling the impeller position in accordance with the invention.

FIGS. 5 to 6 illustrate a method for controlling voltages applied to a stator in order to provide a desired rotation for a permanent magnet rotor (e.g. the impeller) 52 is a field oriented control (FOC) algorithm, which is also known as vector control. It is known in FOC that the stator magnetic field should generally lead the impeller position by 90° for maximum torque efficiency. The magnitude of the attractive force on the impeller is proportional to the magnitude of the phase currents in the stator. Phase current is adjusted by the FOC algorithm according to torque demands for the pump. Since the commutation angle is typically fixed at 90°, the resulting attractive force varies according to torque output from the pump. The exemplary technique varies the $I_d$ current which creates magnetic flux responsible for attracting the impeller. This provides a convenient and accurate mechanism to create a controlled impeller attractive force.

At any particular combination of the (1) magnitude of the phase current and (2) the speed of the impeller, modifying the commutation angle for generating the phase voltages can change the attractive force generated by the stator thereby affecting the impeller balance. In turn, the impeller moves until it settles at a new balanced position where the hydrodynamic forces and magnetic forces are balanced.

FIGS. 5, 6, 7a, and 7b illustrate an exemplary system in accordance with aspects of the invention. Based on the principle of motor vector control, the torque current that is usually called quadrature current ($I_q$ current) and stator coil flux current that is called direct current ($I_d$ current) can be decoupled and controlled independently. The quadrature current $I_q$ current is used to control the impeller rotational speed. The direct $I_d$ current controls the magnetic flux of electromagnetic coils.

In accordance with the invention, $I_d$ current is utilized to control the impeller position by enhancing or weakening the magnetic flux between impeller (rotor) and motor stator coils to adjust the attraction force $F_{em}$. This in turn changes the impeller position (shown in FIG. 6).

In one embodiment, the impeller position control technique is implemented as an open loop control without impeller position sensors. In one embodiment, impeller position control technique is implemented as a closed loop control with impeller position sensors.

In order to ensure proper positioning, active monitoring and control of the impeller position has been employed in the exemplary embodiment by adjusting the stationary magnetic field. However, position sensors and an adjustable magnetic source occupy a significant amount of space and add to the complexity of a system. Accordingly, the use of sensors may depend on the design requirements. Suitable sensors may include, but are not limited to, Hall-effect sensors, variable reluctance sensors, and accelerometers.

Figure 7A:
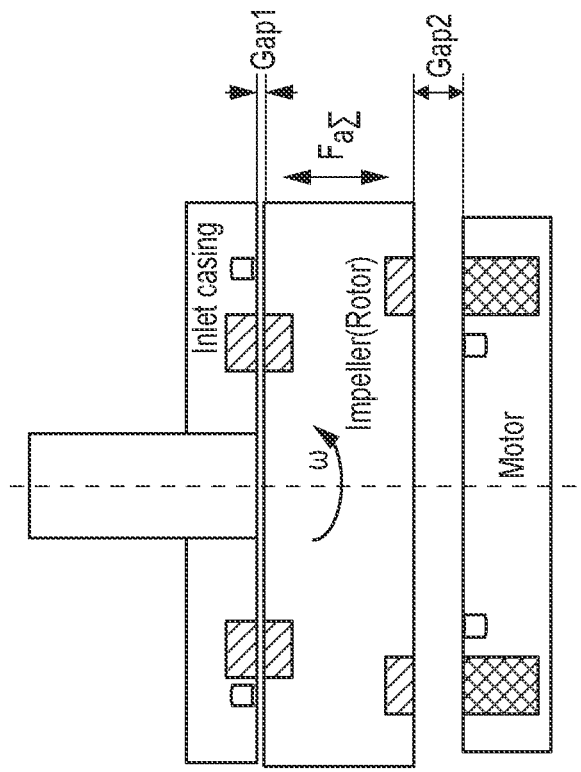
FIG. 7a is a schematic view of the pump of FIG. 1, illustrating the impeller moved to another eccentric position at the bottom of the pump chamber.
Figure 7B:
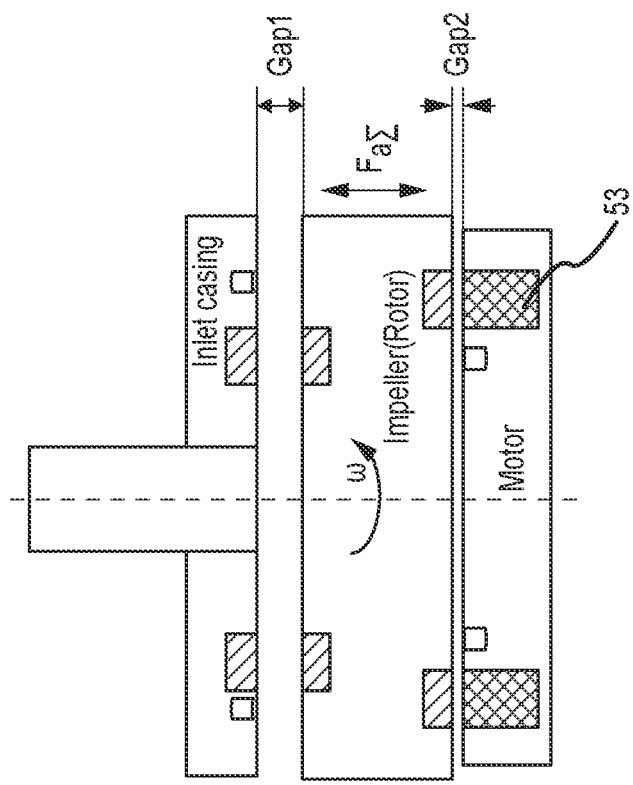
FIG. 7b is a schematic view of the pump of FIG. 1, illustrating the impeller moved to yet another eccentric position at the top of the pump chamber.

In one embodiment using the open loop control, the impeller is controlled by periodically alternating the position from one side to another (e.g. from inlet side to motor side) by modulating the $I_d$ current as shown in FIG. 6. In this manner, the side gaps (Gap 1 and Gap 2) as shown in FIGS. 7a and 7b can be increased or decreased.

The position control technique can be implemented into the hardware and/or software of the system. Referring to FIG. 5, by example, the controller may employ FOC to supply a multiphase voltage signal to the stator assembly 53. The exemplary stator assembly is a three-phase stator. Individual phases a, b, and c and currents $I_a$, $I_b$, and $I_c$ may be driven by an H-bridge inverter functioning as a commutation circuit driven by a pulse width modulator (PWM) circuit. An optional current sensing circuit associated with the inverter measure instantaneous phase current in at least two phases providing current signals designated $I_a$ and $I_b$. A current calculating block receives the two measured currents and calculates a current $I_c$ corresponding to the third phase. The measured currents are input to Vector Control (FOC) block 54 and to a current observer block (not shown) which estimates the position and speed of the impeller. The impeller position and speed are input to the FOC block from speed control block 55 and position control block 56. A target speed or revolutions per minute (rpm) for operating the pump is provided by a conventional physiological monitor to FOC block 54. The target rpm may be set by a medical caregiver or determined according to an algorithm based on various patient parameters such heart beat, physiological needs, suction detection, and the like. FOC block 54 and drive electronics 57 generate commanded voltage output values Va, Vb, and Vc. The Va, Vb, and Vc commands may also be coupled to the observer block for use in detecting speed and position.

The exemplary system differs from conventional configurations inasmuch as the FOC block and electronics are configured to alter the field oriented control algorithm so that a direct current (Id) can be varied independently and generate a desired attractive force.

Figure 8:
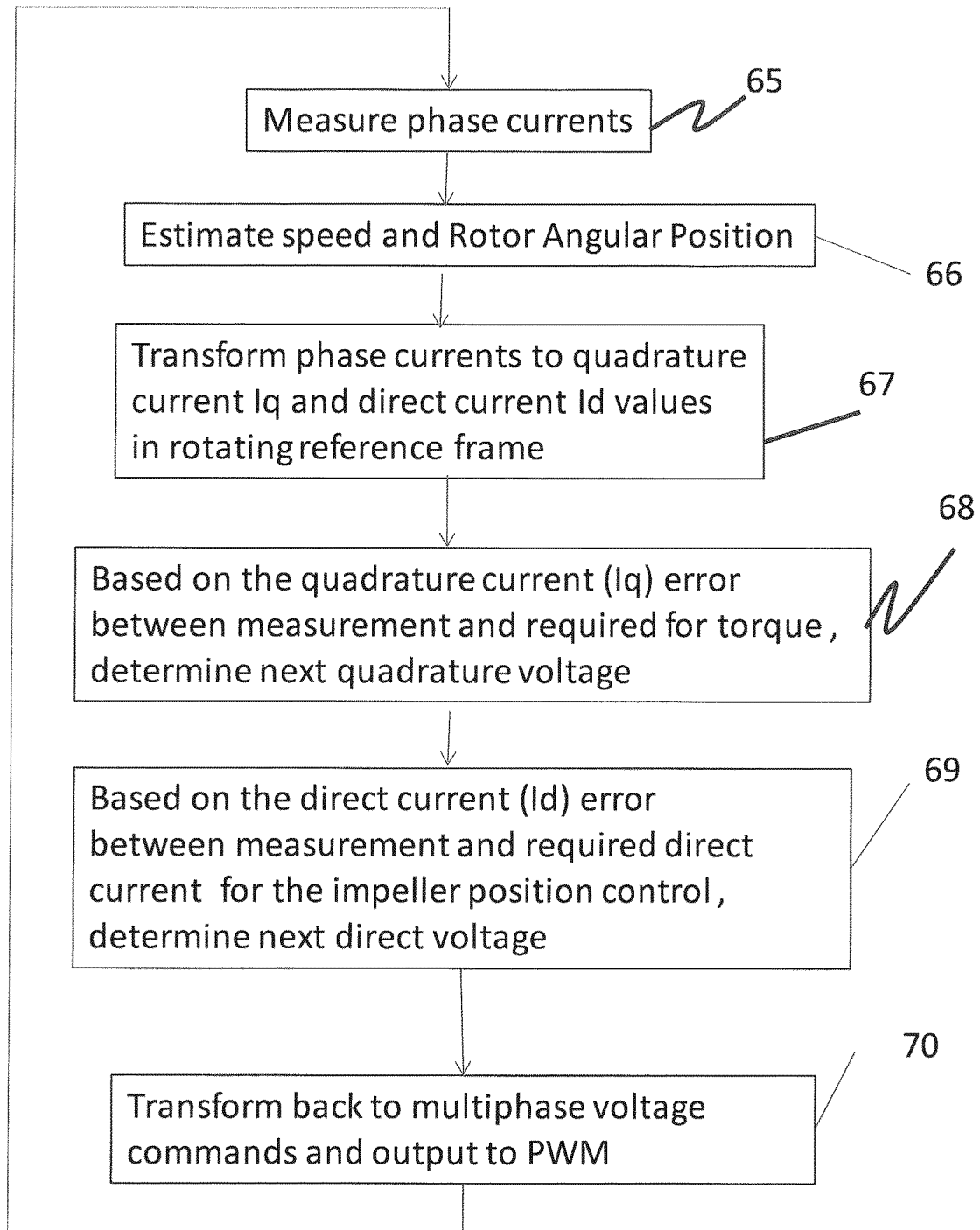
FIG. 8 is a flowchart showing a method of controlling impeller position in accordance with the invention.

In one embodiment, the invention proceeds according to a method as shown in FIG. 8 which highlights a portion of the impeller position control with the field oriented control algorithm. Thus, in step 65 the phase currents are measured. Based on the measured phase currents, the current speed and rotor angle of the impeller are estimated in step 66. Based on the measured rotor angle in step 66, the phase currents are transformed into a two-axis coordinate system to generate quadrature current ($I_q$ current) and direct current ($I_d$) values in a rotating reference frame in step 67. Quadrature current is used to control the torque to rotate the impeller and direct current is used to control the attraction force between rotor and stator to control the impeller position. In step 68, the next quadrature voltage is determined by the quadrature current error between the quadrature current transformed from step 67 and the required current for impeller rotation. In step 69, the next direct voltage is determined by the direct current error between the direct current transformed from step 67 and the required current for the attraction force alternation to control the impeller position. In step 70, the quadrature and direct voltages are transformed back to the stationary reference frame in order to provide the multiphase voltage commands which are output to the PWM circuit.

Figure 9A:
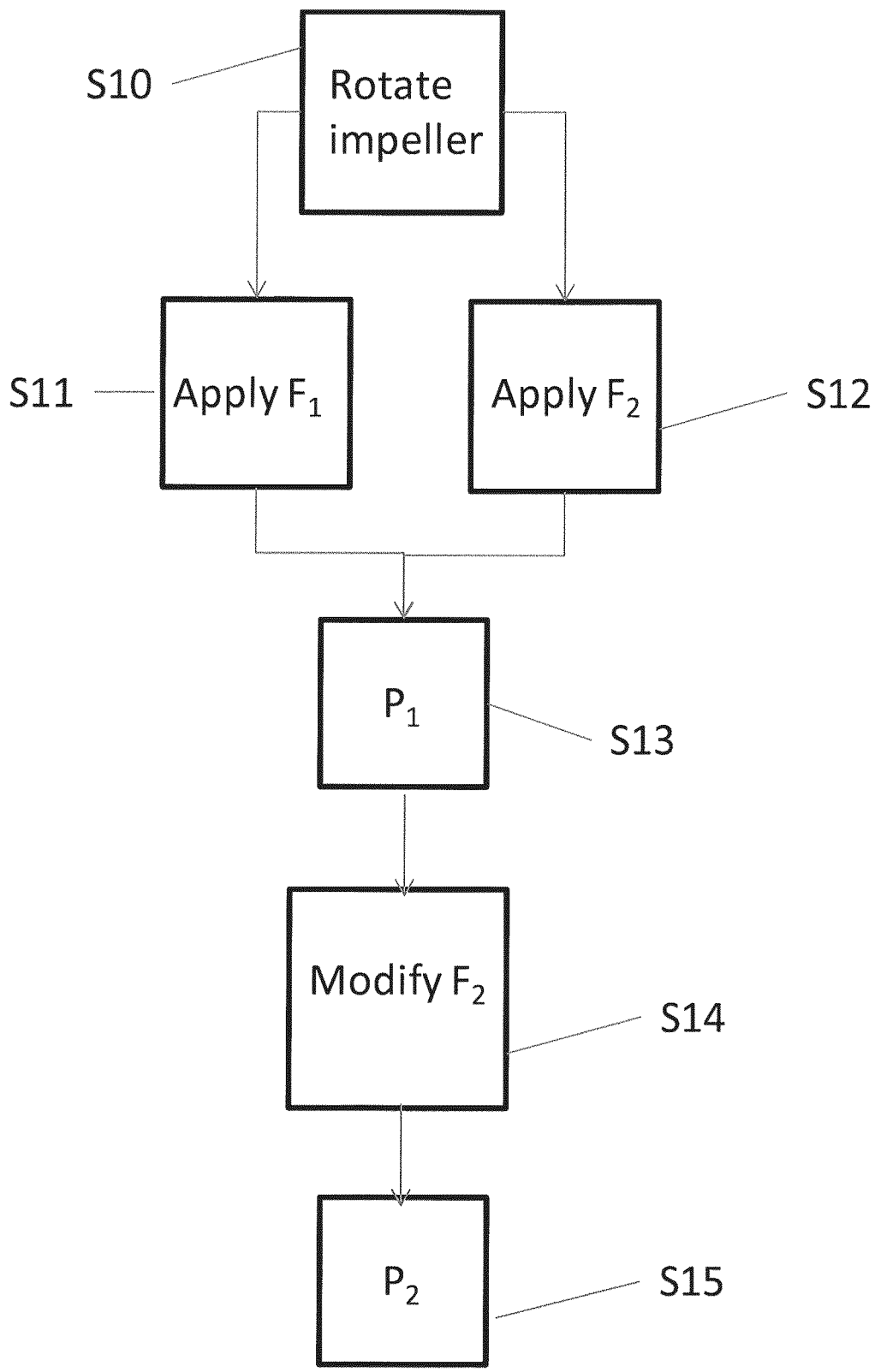
FIG. 9a is a flowchart showing a method of controlling impeller position in accordance with the invention.

FIG. 9a is a flowchart showing another method of operating a rotary machine in accordance with the invention. The method includes operating the pump to rotate the impeller by applying a rotating magnetic field in step S10. During operation the impeller is levitated and positioned at a balanced position ($P_1$) by a balancing of forces. As described above, in an exemplary embodiment the impeller is levitated by the combination of hydrodynamic forces $F_1$ and other bearing forces $F_2$ (e.g. stator attractive force, passive magnetic forces, and/or bulk forces like gravity) in steps S11 and S12. Next, at least one of the forces, $F_2$, is modified to place the impeller out of balance in step S14. The impeller moves to a new position, $P_2$, where the forces are once again balanced in step S15.

As described above, the impeller is moved from the first balanced position ($P_1$) to the second balanced position ($P_2$) by applying an attractive force or modifying (increasing or decreasing) an existing attractive force on the impeller. In various embodiments, the attractive force modulation is substantially continuously applied to hold the impeller in the second balanced position. In various embodiments, the attractive force modulation is applied periodically (e.g. as pulses) to hold the impeller in the second balanced position. In various embodiments, the attractive force modulation is applied as a single pulse to move the impeller in the second balanced position. The second balanced position can be configured so the impeller remains in the second balanced position in a stable manner even when the attractive force is removed.

Figure 9B:
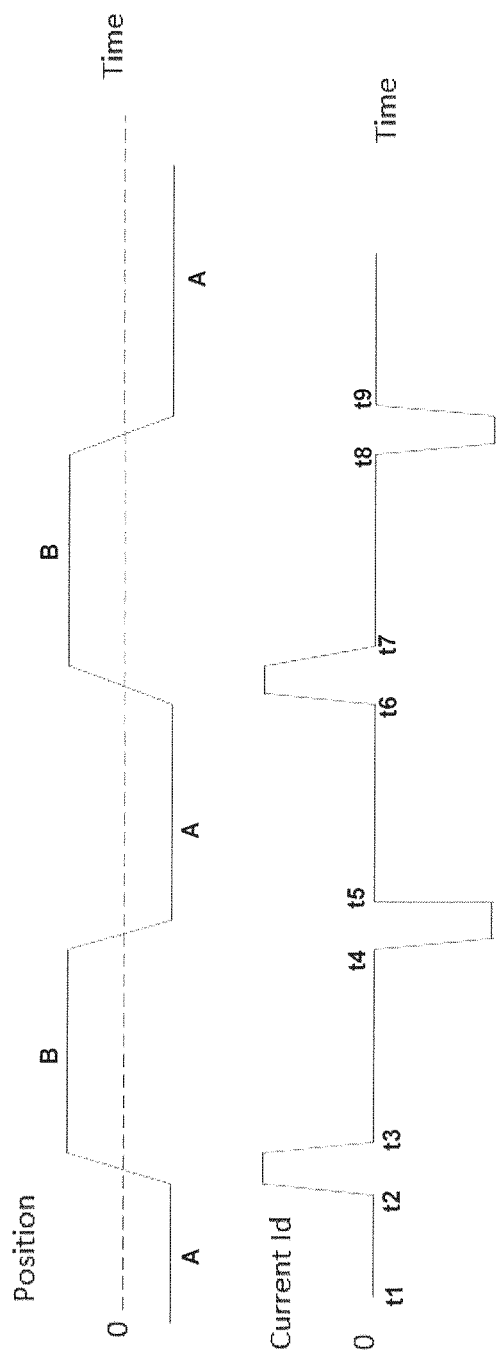
FIG. 9b is a line chart depicting a method for moving the impeller between two balanced positions in accordance with aspects of the invention.

FIG. 9b illustrates an exemplary method for moving the impeller between two balanced positions in accordance with aspects of the invention. In this example, a permanent magnet arrangement is contemplated whereby the two balanced positions are naturally a product of the permanent magnet arrangement, so that the above-mentioned attractive force modulation may not necessarily be needed or required to hold the impeller in a particular balanced position. Rather, a single (or series) pulse may be applied to "push" the impeller from one stable position to another. For example, as shown in FIG. 9b, the impeller is initially, at a time t1, at a stable balanced position A. At a time t2 a pulse of duration (t3–t2) is applied to push the impeller to a new, stable balanced position B. In practice, the impeller may be pushed between stable balanced position A and stable balanced position B in a manner as needed or desired, such as shown in FIG. 9b. Advantageously, such an implementation may save energy and improve pump efficiency. In one embodiment, one of the two stable positions may be relatively close to the inlet of the above mentioned centrifugal pump unit, and another relatively close to the motor.

Figure 10:
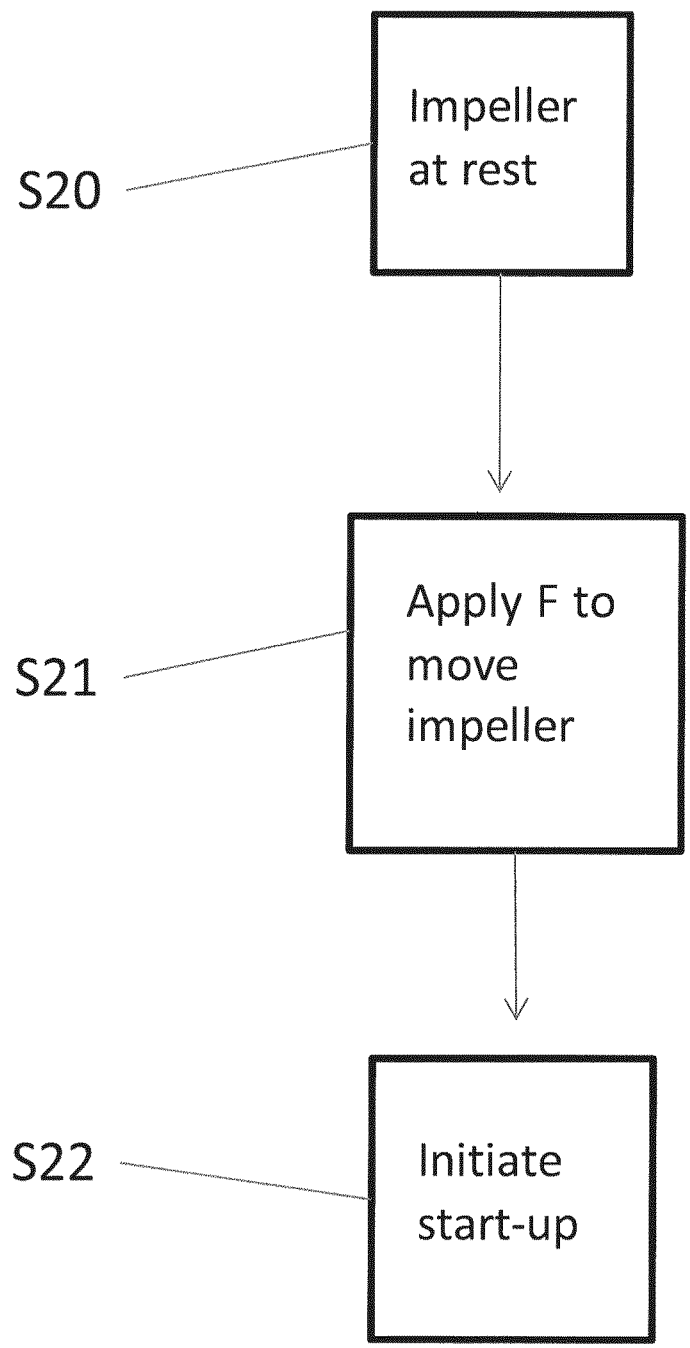
FIG. 10 is a flowchart showing a method of controlling impeller position during start-up of the pump in accordance with the invention.

Turning to FIG. 10, in one embodiment, the impeller position control technique is used to facilitate start-up of the pump. In step S20, the exemplary pump is configured so the impeller rests against the inlet side (top of the housing) when the impeller is not rotating. In a typical pump with hydrodynamic forces alone, or in combination with magnetic forces, the impeller is levitated away from the wall as it rotates. The blood entrained in the gap between the impeller and the house creates hydrodynamic pressure; however, the impeller must be rotating at a sufficient speed to create the hydrodynamic pressure. Until the minimum speed is met, the impeller rubs against the housing wall. In the exemplary pump, by contrast, the impeller is pulled away from the wall prior to, or just after, rotation begins thereby eliminating the deleterious effects of friction. The impeller is pulled away from the wall by applying a force, F, as described above in step S21. For example, the commutation angle may be modified to exert an attractive force. Referring to FIG. 7b, by example, the pump can be configured so the impeller rests at the inlet side. By applying an attractive force to the motor side the impeller moves down from the top wall. In step S22, the regular start-up sequence is initiated after the impeller is removed from the wall.

Figure 11:
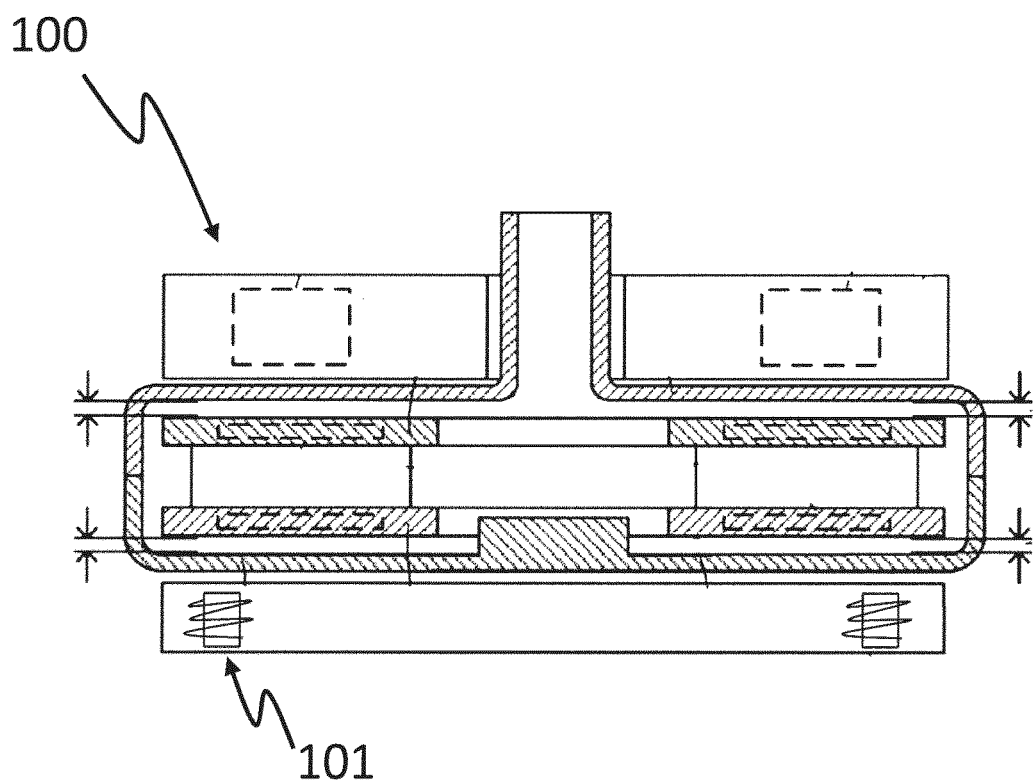
FIG. 11 is a cross-sectional view of an exemplary centrifugal flow pump in accordance with aspects of the invention, illustrating electromagnetic bearings to supplement the stator assembly positioning control.

FIG. 11 shows a rotary machine in accordance with another embodiment making use of electromagnets. Pump 100 in FIG. 11 is similar in various respects to pump 10 in FIG. 3. In the exemplary embodiment, however, pump 100 includes an active electromagnetic (EM) system 1010. The EM force generated by electromagnets is used primarily or adjunctively to move the impeller. Exemplary electromagnets 101 comprise iron cores and windings. The EM force is modified in a conventional manner by changing the current applied to the windings. The application of the EM force causes the impeller to move to position $P_{E2}$. One will appreciate that the EM force can overpower hydrodynamic and passive magnetic forces present in the system. Accordingly, the EM structure must be dimensioned and configured to apply a relatively balanced force. An advantage of using electromagnets over the existing stator assembly is that there is relatively greater positional control over the impeller. By contrast, as described above, the phase currents typically cannot be used as the primary variable to adjust the axial attractive force on the impeller. A disadvantage of this embodiment is the need to provide an entirely separate EM system. This may not be an issue with large industrial rotary machines, but many types of motors have restrictive form factors. For example, implanted pumps must be relatively small in order to address a wider patient population.

Figure 12:
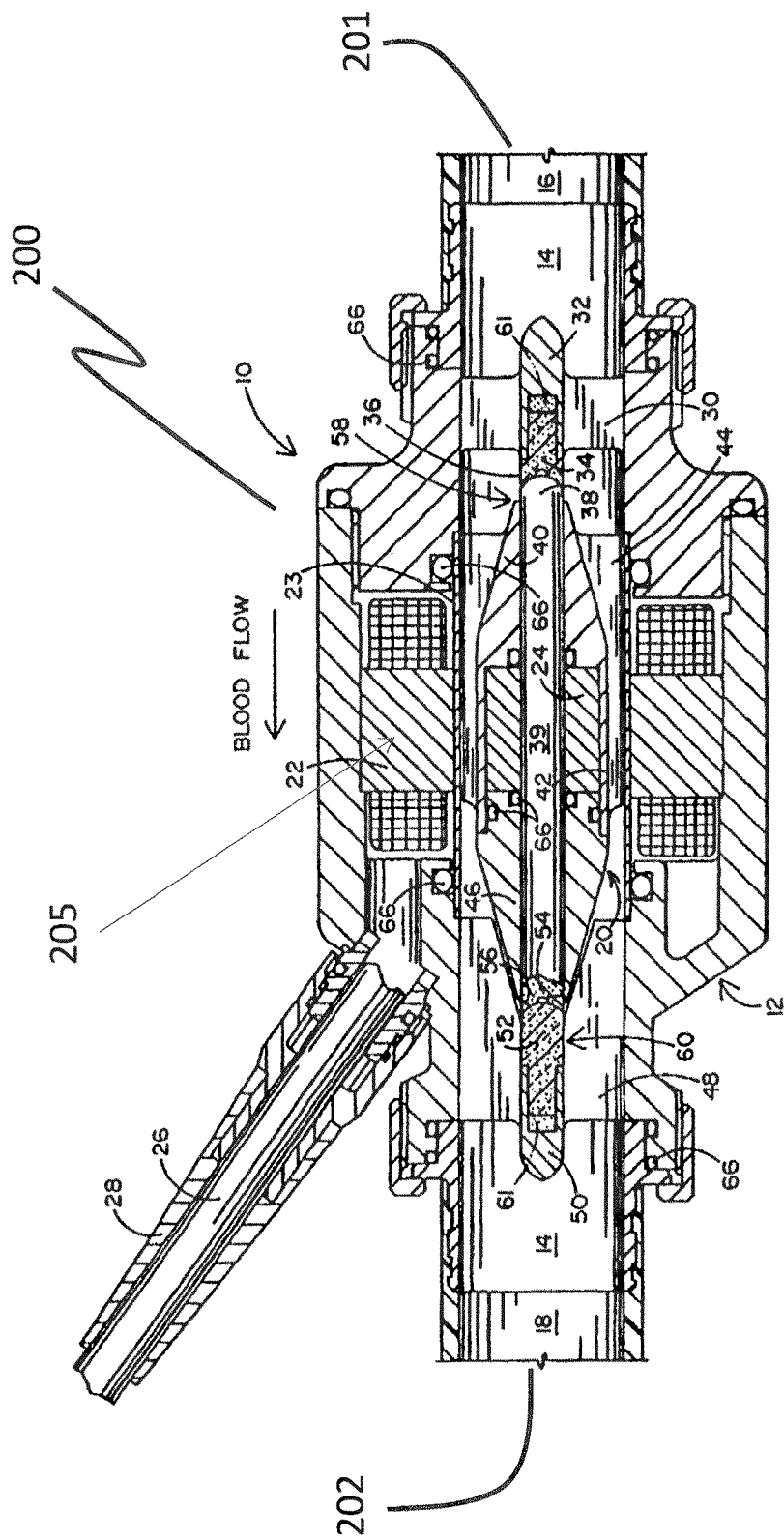
FIG. 12 is a cross-sectional view of an axial flow pump in accordance with aspects of the invention, the axial flow pump including mechanical bearings.
Figure 13:
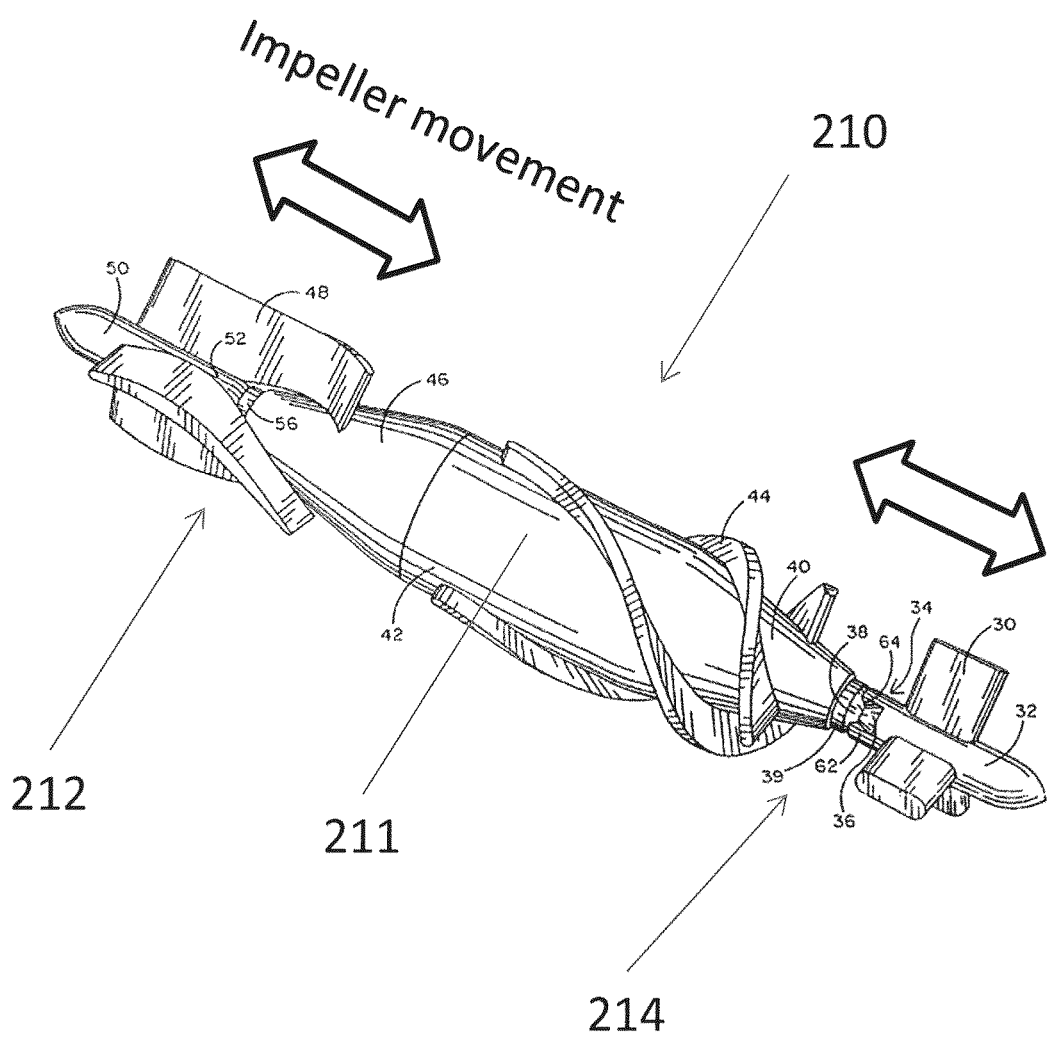
FIG. 13 is a perspective view of the impeller of FIG. 12, with arrows depicting the direction of translation in accordance with the invention.

FIGS. 12 and 13 illustrate another implantable pump in accordance with the invention. Pump 200 is similar in various respects to pumps 10 and 100 described above except pump 200 is an axial flow pump. Blood flows from in through inlet 201 and out through outlet 202 in a generally linear, axial direction. Pump 200 includes an impeller 210 having blades for moving blood through the pump housing and imparting kinetic energy in the fluid.

Impeller 210 is fixed within the housing by ball-and-cup bearings 212 and 214. The ball-and-cup bearings are closely toleranced and generally fix the impeller in a specific position. However, the exemplary bearings are lubricated and washed by the blood flow around the impeller. Accordingly, there is some fluid between the ball and cup surfaces.

Torque is applied to the impeller by a stator assembly 205. The stator assembly 205 includes windings and is driven using a FOC algorithm in a similar manner to the stator assemblies described above. In practice, the impeller position is adjusted proceeding according to the method shown in FIG. 9. Using the FOC technique described above the impeller is rotated in the pump housing. At a desired time the $I_d$ current is modulated to adjust the attractive force on the impeller in the axial direction. As long as the attractive force is sufficient to squeeze blood out from a respective bearing gap, the impeller will move axially towards inlet 201 or outlet 202. The bearing gaps of pump 200 are relatively small compared to Gap 1 and Gap 2 of pump 50 in FIG. 4. However, even relatively small impeller movement may be beneficial to enable control of the bearing gaps.

Figure 14:
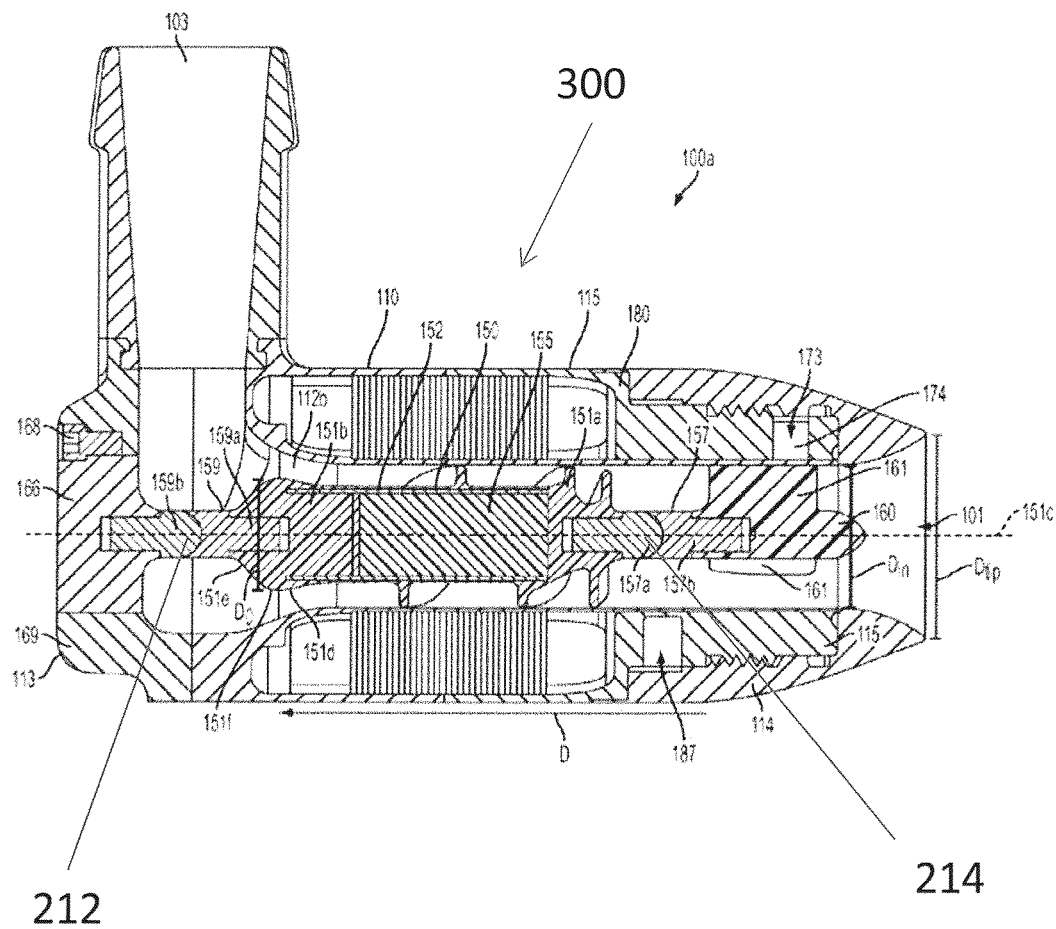
FIG. 14 is a cross-sectional view of another axial flow pump in accordance with aspects of the invention, the axial flow pump including mechanical bearings.

FIG. 14 illustrates another pump 300 similar to pump 200. Pump 300 includes an impeller fixed between two mechanical bearings 212 and 214. Pump 300 is slightly different than pump 200 because the outlet extends at an angle from the inlet. Pump 300 is configured in a relatively compact design compared to pump 200 including a relatively smaller stator assembly; however, the same general principles can be applied to control the motor and adjust the impeller position.

Figure 15:
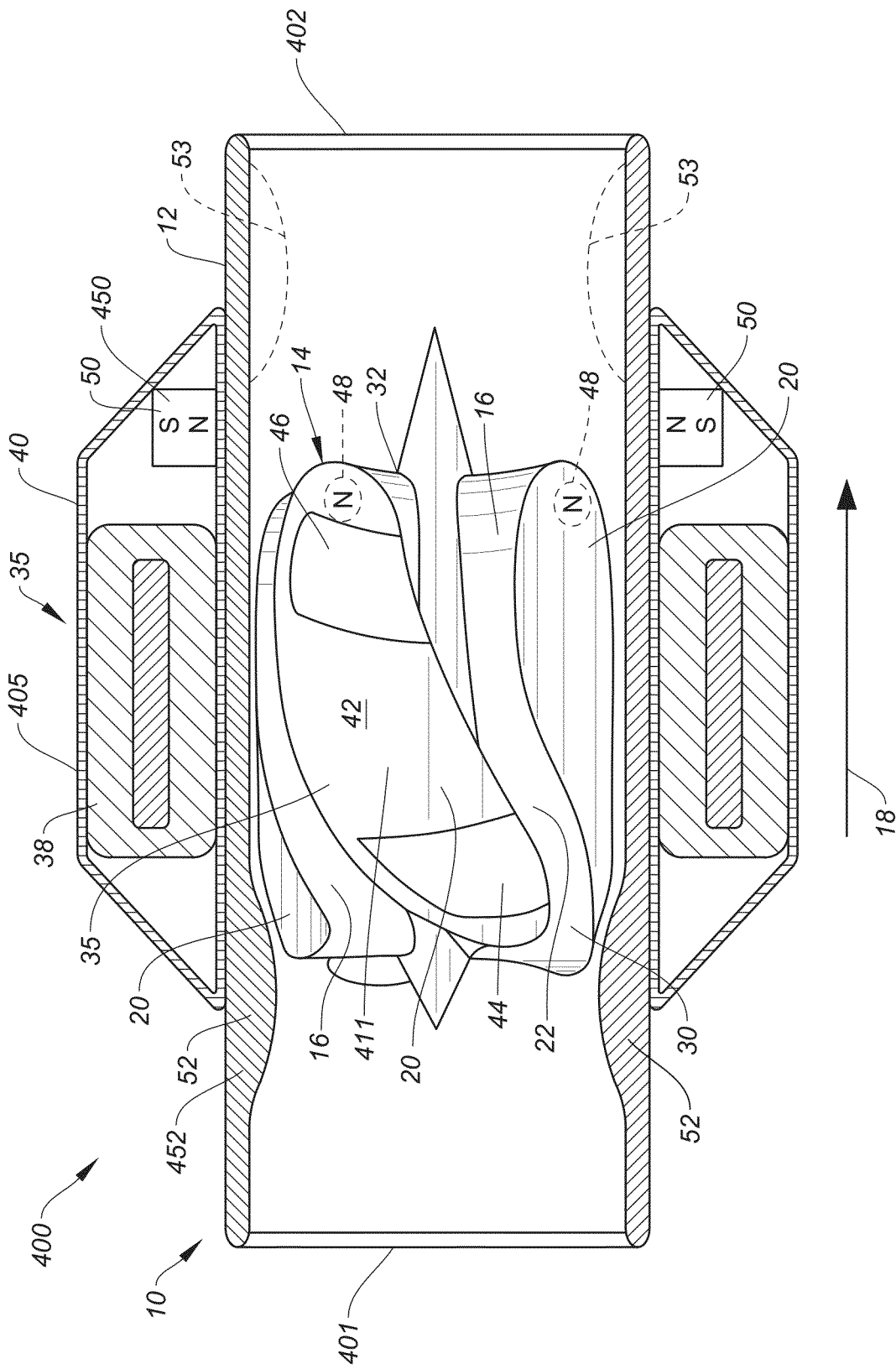
FIG. 15 is a cross-sectional view of another axial flow pump in accordance with aspects of the invention, the axial flow pump including passive magnetic and hydrodynamic bearings.

FIG. 15 is a cross-sectional view of another pump 400 similar to pumps 200 and 300, except pump 400 is an axial flow pump with non-contact bearings. Pump 400 includes a pump housing having an inlet 401 and outlet 402. An impeller 411 is positioned within a pump chamber for imparting flow to the blood fluid within the housing. The impeller is entirely formed of a magnetic material which is driven by interaction with a stator assembly 405.

Impeller 411 is stabilized in the pump chamber by a combination of hydrodynamic and passive magnetic forces. Impeller 411, which is a magnetic material, interacts with the magnetic material in stator assembly 405 to provide an axial centering force. A pump ring 452 with a chamfer surface is positioned at the leading end of the impeller to create hydrodynamic stabilization forces in the axial direction (left to right) and radial direction (up and down on page). A permanent magnet ring 450 is provided at the trailing edge of the impeller is oriented with a north pole facing a north pole of the impeller. This arrangement creates an axial bias force to push the impeller against the pump ring 452. The magnet ring 450 also provides a radially centering force. Finally, the impeller includes deep hydrodynamic grooves to generate a hydrodynamic pressure force against the inner walls of the pump chamber for radial stabilization.

In operation, the impeller remains stable in the axial and radial directions. There may be some axial movement as the rotational speed of the impeller changes or as a result of other forces (e.g. the native pulse), but generally the impeller remains centered below the stator assembly.

Using the FOC control technique described above, the attractive force of the stator assembly 405 on impeller 411 can be modified. In one embodiment, pump 400 is configured so impeller is eccentric when centered below the stator assembly 405. In this example, increasing the attractive force amounts to an increase in the axial stiffness to resist axial movement. In one embodiment, the attractive force is modified to actually move impeller 411 axially. For example, the impeller can be moved closer to pump ring 452 to squeeze blood out of the gap between impeller 411 and a surface of ring 452. The impeller may also be moved away from ring 452 to increase the blood gap therebetween.

In this manner, the impeller position control technique adds an element of active position control otherwise not possible with the passive bearing configuration of pump 400.

Although aspects of the invention have been described in connection with blood pumps, one will appreciate from the description herein that the invention can be applied equally to other types of rotary machines such as washing machines, manufacturing machines, computer drives, and more.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A blood pump, comprising:
an impeller disposed within a housing, the housing comprising an inlet for receiving blood from a patient, the inlet being positioned at a first side of the impeller;
a stator positioned at a second side of the impeller opposite the first side; and
a controller that is electrically coupled with the stator, wherein the controller is configured to:
prior to starting up rotation of the impeller, adjust a stator coil flux current provided to the stator to move the impeller in an axial direction from a resting position to a position in which the impeller is moved away from an inner surface of the housing, wherein:
in the resting position, a side of the impeller rests against the inner surface of the housing;
supply a torque current to the stator to rotate the impeller within the housing upon moving the impeller to the position; and
periodically alternate a position of the impeller between an inlet side position and a stator side position by adjusting the stator coil flux current, wherein:
in the inlet side position, a first gap between the impeller and an inlet side of the housing is smaller than a second gap between the impeller and a motor side of the housing;
in the stator side position, the first gap is greater than the second gap; and
periodically alternating the position of the impeller comprises holding the impeller at a respective one of the inlet side position and the stator side position for a period of time before each adjustment of the stator coil flux to move the impeller to the other one of the inlet side position and the stator side position.

2. The blood pump of claim 1, wherein:
the inner surface comprises an inlet side of the housing.

3. The blood pump of claim 1, wherein:
the controller is further configured to adjust the stator coil flux current provided to the stator to move the impeller in the axial direction from the inlet side position to the stator side position.

4. The blood pump of claim 1, wherein:
the inner surface and an additional inner surface of the housing each define hydrodynamic pressure grooves facing the impeller.

5. The blood pump of claim 1, wherein:
the impeller defines one or more hydrodynamic pressure grooves.

6. The blood pump of claim 1, further comprising:
one or more sensors for monitoring an axial position of the impeller, wherein the controller is further configured to adjust the stator coil flux current based on a measurement from the one or more sensors.

7. The blood pump of claim 1, wherein:
the period of time is greater than a period of time of movement of the impeller from one of the inlet side position and the stator side position to the other of the inlet side position and the stator side position.

8. A method of operating a blood pump, comprising:
adjusting a stator coil flux current provided to a stator of the blood pump to move an impeller of the blood pump in an axial direction from a resting position to a position in which the impeller is moved away from an inner surface of a housing of the blood pump prior to starting up rotation of the impeller, wherein:
the housing comprises an inlet for receiving blood from a patient, the inlet being positioned at a first side of the impeller;
the stator is positioned at a second side of the impeller opposite the first side; and
in the resting position, a side of the impeller rests against the inner surface of the housing of the blood pump;
supplying a torque current to the stator to rotate the impeller within the housing upon moving the impeller to the position; and
periodically alternate a position of the impeller between an inlet side position and a stator side position by adjusting the stator coil flux current, wherein:
in the inlet side position, a first gap between the impeller and an inlet side of the housing is smaller than a second gap between the impeller and a motor side of the housing;

in the stator side position, the first gap is greater than the second gap; and periodically alternating the position of the impeller comprises holding the impeller at a respective one of the inlet side position and the stator side position for a period of time before each adjustment of the stator coil flux to move the impeller to the other one of the inlet side position and the stator side position.

9. The method of operating a blood pump of claim 8, wherein:

adjusting the stator coil flux current comprises applying an initial stator coil flux current.

10. The method of operating a blood pump of claim 8, wherein:

adjusting the stator coil flux current comprises increasing or reducing an existing stator coil flux current.

11. The method of operating a blood pump of claim 8, wherein:

the torque current and stator coil flux current are independently controllable.

12. The method of operating a blood pump of claim 8, wherein:

adjusting the stator coil flux current comprises modifying a commutation angle of a phase voltage supplied to the stator.

13. The method of operating a blood pump of claim 8, wherein:

periodically alternating the position of the impeller between the inlet side position and the stator side position by adjusting the stator coil flux current comprises modifying the stator coil flux current in a single pulse.

14. A non-transitory machine readable medium having instructions stored thereon, wherein the instructions, when executed, cause at least one processor to perform operations comprising:

adjusting a stator coil flux current provided to a stator of a blood pump to move an impeller of the blood pump in an axial direction from a resting position to a balanced position in which the impeller is moved away from an inner surface of a housing of the blood pump prior to starting up rotation of the impeller, wherein:

the housing comprises an inlet for receiving blood from a patient, the inlet being positioned at a first side of the impeller;

the stator is positioned at a second side of the impeller opposite the first side; and in the resting position, a side of the impeller rests against the inner surface of the housing of the blood pump;

supplying a torque current to the stator to rotate the impeller within the housing upon moving the impeller to the position; and periodically alternating a position of the impeller position between an inlet side position and a stator side position by adjusting the stator coil flux current, wherein:

in the inlet side position, a first gap between the impeller and an inlet side of the housing is smaller than a second gap between the impeller and a stator side of the housing;

in the stator side position, the first gap is greater than the second gap; and periodically alternating the position of the impeller comprises holding the impeller at a respective one of the inlet side position and the stator side position for a period of time before each adjustment of the stator coil flux to move the impeller to the other one of the inlet side position and the stator side position.

15. The non-transitory machine readable medium of claim 14, wherein the instructions further cause the at least one processor to:

continuously modify the stator coil flux current to move the impeller from the inlet side position to the motor stator side position and to hold the impeller in the stator side position.

16. The non-transitory machine readable medium of claim 14, wherein:

after the impeller has moved to the inlet side position, modifying the stator coil flux current is not required to maintain the impeller in the inlet side position.

17. The non-transitory machine readable medium of claim 14, wherein:

supplying the torque current to the stator to rotate the impeller comprises using a field oriented control algorithm.

* * * * *